(12) United States Patent
Burnett, Jr.

(10) Patent No.: US 11,072,642 B2
(45) Date of Patent: Jul. 27, 2021

(54) MANP ANALOGUES

(71) Applicant: Mayo Foundation for Medical Education and Research, Rochester, MN (US)

(72) Inventor: John C. Burnett, Jr., Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 16/348,652

(22) PCT Filed: Nov. 9, 2017

(86) PCT No.: PCT/US2017/060808
§ 371 (c)(1),
(2) Date: May 9, 2019

(87) PCT Pub. No.: WO2018/089601
PCT Pub. Date: May 17, 2018

(65) Prior Publication Data
US 2019/0352364 A1 Nov. 21, 2019

Related U.S. Application Data

(60) Provisional application No. 62/419,611, filed on Nov. 9, 2016.

(51) Int. Cl.
*A61K 38/00* (2006.01)
*C07K 14/58* (2006.01)
*A61P 9/12* (2006.01)
*A61P 13/12* (2006.01)

(52) U.S. Cl.
CPC .......... *C07K 14/58* (2013.01); *A61P 9/12* (2018.01); *A61P 13/12* (2018.01); *C07K 14/582* (2013.01); *A61K 38/00* (2013.01)

(58) Field of Classification Search
None
See application file for complete search history.

(56) References Cited

U.S. PATENT DOCUMENTS

| | | |
|---|---|---|
| 4,161,521 A | 7/1979 | Veber et al. |
| 4,728,721 A | 3/1988 | Yamamoto et al. |
| 4,757,048 A | 7/1988 | Lewicki et al. |
| 4,935,492 A | 6/1990 | Lewicki et al. |
| 4,938,763 A | 7/1990 | Dunn et al. |
| 5,226,325 A | 7/1993 | Komurasaki et al. |
| 5,278,201 A | 1/1994 | Dunn et al. |
| 5,278,202 A | 1/1994 | Dunn et al. |
| 5,410,016 A | 4/1995 | Hubbell et al. |
| 5,501,863 A | 3/1996 | Rössling et al. |
| 5,529,914 A | 6/1996 | Hubbell et al. |
| 5,580,859 A | 12/1996 | Felgner et al. |
| 5,589,466 A | 12/1996 | Felgner et al. |
| 5,698,213 A | 12/1997 | Jamiolkowski et al. |
| 6,312,679 B1 | 11/2001 | Tomalia et al. |
| 6,410,044 B1 | 6/2002 | Chudzik et al. |
| 7,803,901 B2 | 9/2010 | Burnett et al. |
| 8,063,191 B2 | 11/2011 | Burnett et al. |
| 2004/0086976 A1 | 5/2004 | Fleer et al. |
| 2010/0266704 A1 | 10/2010 | Ahlheim et al. |
| 2014/0066367 A1 | 3/2014 | Chen et al. |

FOREIGN PATENT DOCUMENTS

| | | |
|---|---|---|
| EP | 0045665 | 2/1982 |
| WO | WO 93/16687 | 9/1993 |
| WO | WO 2004/047871 | 6/2004 |
| WO | WO 2004/071736 | 8/2004 |
| WO | WO 2006/017852 | 2/2006 |
| WO | WO 2008/061355 | 5/2008 |
| WO | WO 2011/005939 | 1/2011 |
| WO | WO 2016/077143 | 5/2016 |

OTHER PUBLICATIONS

US 6,884,780 B2, 04/2005, Drummond et al. (withdrawn)
Morris and Weiss, Combinatorial Alanine Scanning, Current Opinion in Chemical Biology (2001), 5:302-307 (Year: 2001).*
Parker, A.S., et al, Optimization of Combinatorial Mutagenesis, Journal of Computational Biology (2001), 5:302-307 (Year: 2011).*
Almquist et al., "Synthesis and biological activity of a ketomethylene analog of a tripeptide inhibitor of angiotensin converting enzyme," J. Med. Chem., 23(12):1392-8, Dec. 1980.
Banga, "Theme section: Transdermal delivery of proteins," Pharm. Res., 24(7):1357-9, Jul. 2007.
Buglioni et al., "Structural insights into C-terminus and N-terminus of a designer cGMP activating ANP-based antihypertensive peptide: ZD100," Abstract presented at American Heart Association Meeting Nov. 2016, 1 page, Available on or after Nov. 11, 2016.
Cataliotti et al., "Oral brain natriuretic peptide: A novel strategy for chronic protein therapy for cardiovascular disease," Trends Cardiovasc. Med., 17(1):10-4, Jan. 2007.
Goebel and Neubert, "Dermal peptide delivery using colloidal carrier systems," Skin Pharmacol. Physiol. 21(1):3-9, 2008.
Guatelli et al., "Isothermal, in vitro amplification of nucleic acids by a multienzyme reaction modeled after retroviral replication," Proc. Natl. Acad. Sci. USA, 87(5):1874-8, Mar. 1990.
Hann et al., "On the double bond isostere of the peptide bond: Preparation of an enkephalin analogue," J. Chem. Soc. Perkin Trans. 1, 307-14, Jan. 1982.
Holladay and Rich, "Synthesis of hydroxyethylene and ketomethylene dipeptide isosteres," Tetrahedron Lett., 24(41):4401-4, Jul. 1983.
Hruby, "Conformational restrictions of biologically active peptides via amino acid side chain groups," Life Sci., 31(3):189-99, Jul. 1982.
Hudson et al., "Methionine enkephalin and isosteric analogues I. Synthesis on a phenolic resin support," Int. J. Pept. Prot. Res., 14(3):177-85, Sep. 1979.

(Continued)

*Primary Examiner* — Thomas S Heard
(74) *Attorney, Agent, or Firm* — Fish & Richardson P.C.

(57) ABSTRACT

Analogues of an alternatively spliced form of atrial natriuretic peptide (MANP) that exhibit pGC-A gain of function and can be used to treat cardiorenal and metabolic disease are described herein.

6 Claims, 24 Drawing Sheets

Specification includes a Sequence Listing.

(56) References Cited

OTHER PUBLICATIONS

Jennings-White and Almquist, "Synthesis of ketomethylene analogs of dipeptides," Tetrahedron Lett., 23(25):2533-4, Mar. 1982.
Komatsu et al., "C-type natriuretic peptide (CNP) in rats and humans" Endocrinol., 129(2):1104-6, Aug. 1991.
Kuhn, "Structure, regulation, and function of mammalian membrane guanylyl cyclase receptors, with a focus on guanylyl cyclase-A," Circ. Res., 93(8):700-9, Oct. 2003.
Lebl and Hruby, "Synthesis of cyclic peptides by solid phase methodology," Tetrahedron Lett., 25(20):2067-8, Jan. 1984.
Lewis, "PCR's competitors are alive and well and moving rapidly towards commercialization," Genetic Engineering News, 12(9):1, 1992.
Malik et al., "10.2174/156720107780362339," Curr. Drug Deliv., 4(2):141-51, Apr. 2007.
Miller et al., "Amphiphilic conjugates of human brain natriuretic peptide designed for oral delivery: In vitro activity screening," Bioconjugate Chem., 17(2):267-74, Feb. 2006.
Morley, "K+ channel openers and suppression of airway hyperreactivity," Trends Pharm. Sci., 15(12):463-8, Dec. 1994.
PCT International Preliminary Report on Patentability in International Appln. No. PCT/2017/060808, dated May 23, 2019, 8 pages.
PCT International Search Report and Written Opinion in International Appln. No. PCT/2017/060808, dated Mar. 26, 2018, 13 pages.
Prausnitz, "A peptide chaperone for transdermal drug delivery," Nat. Biotechnol., 24(4):416-7, Apr. 2006.
Schiller et al., "A novel cyclic opioid peptide analog showing high preference for μ-receptors," Biochem. Biophys. Res. Comm., 127(2):558-64, Mar. 1985.
Schiller et al., "Synthesis of side-chain to side-chain cyclized peptide analogs on solid supports," Int. J. Peptide Protein Res., 25(2):171-7, Feb. 1985.
Spatola et al., "Structure-activity relationships of enkephalins containing serially replaced thiomethylene amide bond surrogates," Life Sci., 38(14):1243-9, Apr. 1986.
Spatola, "Peptide backbone modifications: a structure-activity analysis of peptides containing amide bond surrogates, conformational constraints, and related backbone re-placements," Chemistry and Biochemistry of Amino Acids, Peptides, and Proteins, 7:267-357, 1983.
Tawaragi et al., "Gene and precursor structures of human C-type natriuretic peptide," Biochem. Biophys. Res. Commun., 175(2):645-651, Mar. 1991.
Veronese and Mero, "The impact of PEGylation on biological therapies," BioDrugs, 22(5):315-29, Sep. 2008.
Veronese and Pasut, "PEGylation, successful approach to drug delivery," Drug Discov. Today, 10(21):1451-8, Nov. 2005.
Wang et al., "Albubnp, a recombinant B-type natriuretic peptide and human serum albumin fusion hormone, as a long-term therapy of congestive heart failure," Pharm. Res., 21(11):2105-11, Nov. 2004.
Weiss "How LCR works," Science, 254(5036):1292, Nov. 1991.
Wermeling et al., "Microneedles permit transdermal delivery of a skin-impermeant medication to humans," Proc. Natl. Acad. Sci. USA, 105(6):2058-63, Feb. 2008.
Extended European Search Report in European Application No. 17870165.2 dated May 29, 2020, 8 pages.
McKie et al., "A human atrial natriuretic peptide gene mutation reveals a novel peptide with enhanced blood pressure-lowering, renal-enhancing, and aldosterone-suppressing actions," Journal of the American College of Cardiology, 54(11):1024-32, Sep. 2009.
Meems and Burnett, "Innovative therapeutics: designer natriuretic peptides," JACC: Basic to Translational Science, 1(7):557-67, Dec. 2016.

\* cited by examiner

MANP

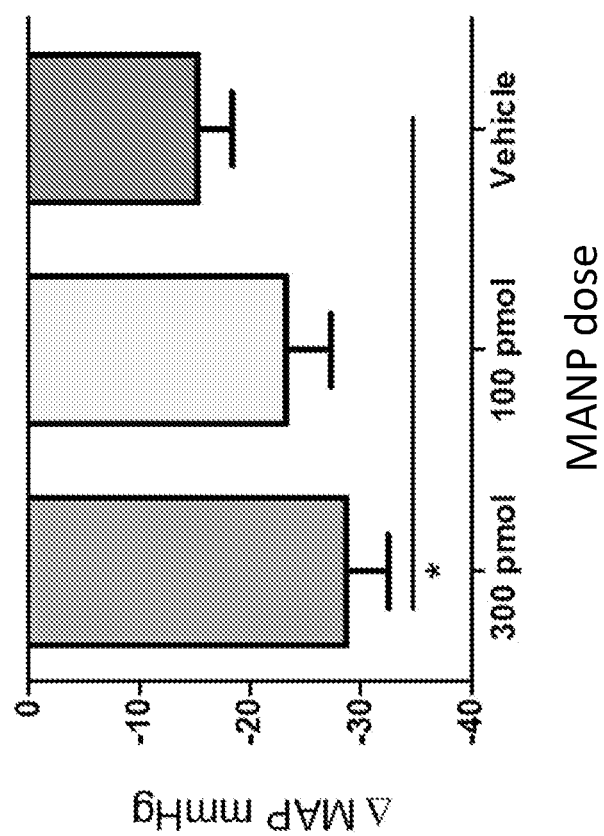

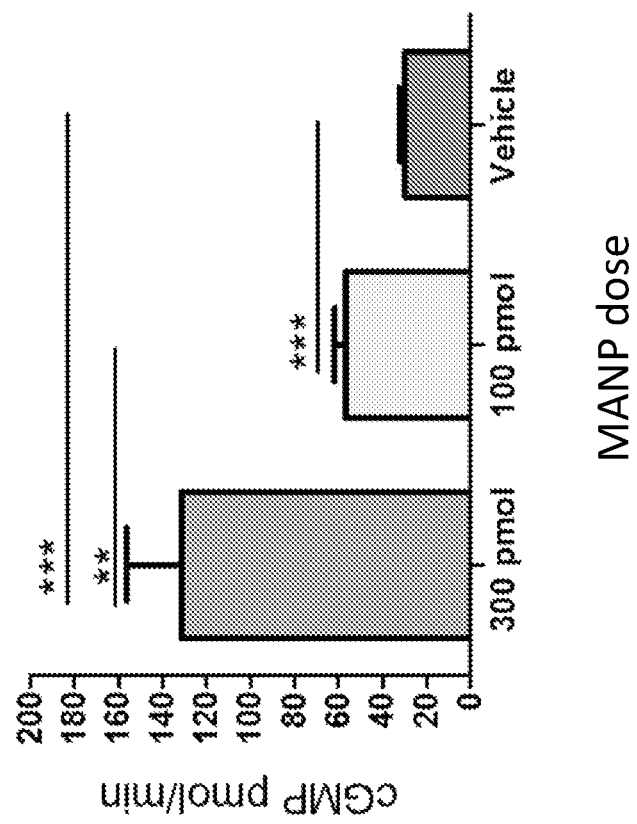

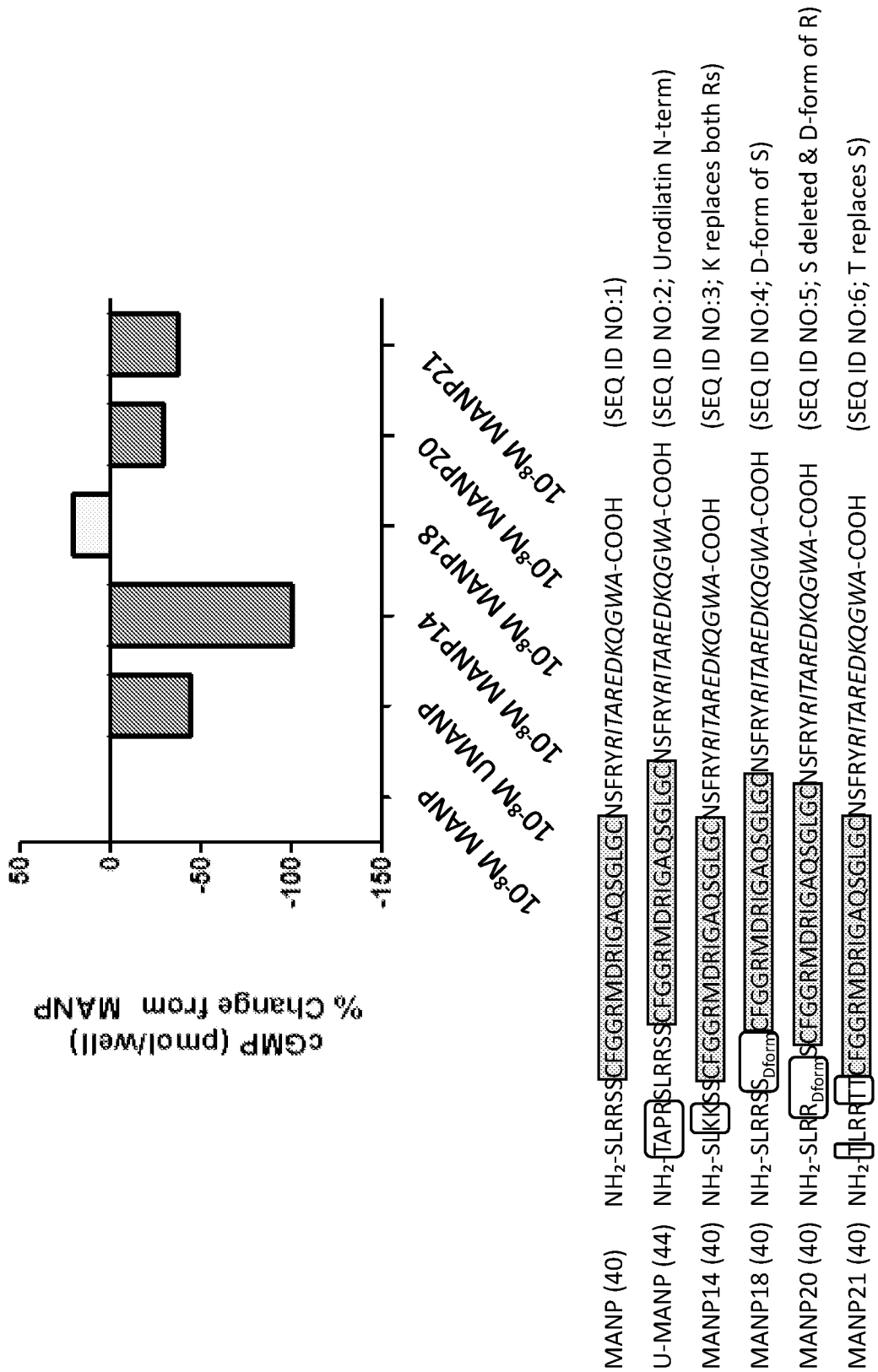

MANP ANALOGUES

CROSS-REFERENCE TO RELATED APPLICATIONS

This application is a National Stage application under 35 U.S.C. § 371 of International Application No. PCT/US2017/060808, having an International Filing Date of Nov. 9, 2017, which claims benefit of priority from U.S. Provisional Application Ser. No. 62/419,611, filed Nov. 9, 2016, which is incorporated herein by reference in its entirety.

STATEMENT AS TO FEDERALLY SPONSORED RESEARCH

This invention was made with government support under HL076611 awarded by the National Institutes of Health. The government has certain rights in the invention.

TECHNICAL FIELD

This document relates to analogues of an alternatively spliced form of atrial natriuretic peptide (MANP), and more particularly to MANP analogues having one or more variations in the N-terminal portion of MANP that can render the analogues more potent in their activation of the pGC-A receptor (also referred to as NPR-A). In addition, this document relates to the use of MANP analogues in the treatment of cardiovascular, cardiorenal, and metabolic disease.

BACKGROUND

Natriuretic polypeptides are polypeptides that can cause natriuresis—increased sodium excretion in the urine. Natriuretic polypeptides can be produced by brain, heart, kidney, and/or vascular tissue. The natriuretic polypeptide family in humans includes the cardiac hormones atrial natriuretic peptide (ANP), B-type natriuretic peptide (BNP), C-type natriuretic peptide (CNP), and urodilatin (URO). Natriuretic polypeptides function via two well-characterized guanylyl cyclase receptors (NPR-A for ANP, BNP, and URO; and NPR-B for CNP) and the second messenger cyclic 3'5' guanosine monophosphate (cGMP) (Kuhn (2003) Circ. Res. 93:700-709; Tawaragi et al. (1991) *Biochem. Biophys. Res. Commun.* 175:645-651; and Komatsu et al. (1991) *Endocrinol.* 129:1104-1106).

SUMMARY

As compared to ANP, MANP is more potent at reducing blood pressure (BP), inducing natriuresis, and inhibiting aldosterone via pGC-A and its second messenger cGMP. This document is based, at least in part, on the development of designer MANP-based peptides that contain modifications within in their N-terminal sequences as compared to MANP. The polypeptides provided herein can that display enhanced activation of the pGC-A receptor as compared to MANP, and in some cases, may be even more effective for treating hypertension (HTN) than MANP.

In one aspect, this document features a natriuretic polypeptide containing the amino acid sequence set forth in SEQ ID NO:1, with the proviso that the polypeptide includes one, two, three, four, or five amino acid additions, subtractions, or substitutions as compared to SEQ ID NO:1, wherein at least one addition, subtraction, or substitution is within positions 1 to 6 of SEQ ID NO:1. The polypeptide can have one to five conservative amino acid substitutions as compared to SEQ ID NO:1, or can have one to three conservative amino acid substitutions as compared to SEQ ID NO:1. The polypeptide can have one or two non-conservative amino acid substitutions as compared to SEQ ID NO:1. The serine at position 6 of SEQ ID NO:1 can be substituted with D-serine (SEQ ID NO:4). The arginine at position 4 of SEQ ID NO:1 can be substituted with D-arginine and the serine at position 5 of SEQ ID NO:1 can be deleted (SEQ ID NO:5). The polypeptide can include the amino acid sequence set forth in SEQ ID NO:2, SEQ ID NO:3, SEQ ID NO:6, or SEQ ID NO:15. The polypeptide can be a substantially pure polypeptide.

In another aspect, this document features an isolated nucleic acid encoding a natriuretic polypeptide that contains the amino acid sequence set forth in SEQ ID NO:1, with the proviso that the polypeptide includes one, two, three, four, or five amino acid additions, subtractions, or substitutions as compared to SEQ ID NO:1, wherein at least one addition, subtraction, or substitution is within positions 1 to 6 of SEQ ID NO: 1.

In another aspect, this document features a vector containing a nucleic acid that encodes a natriuretic polypeptide having the amino acid sequence set forth in SEQ ID NO:1, with the proviso that the polypeptide includes one, two, three, four, or five amino acid additions, subtractions, or substitutions as compared to SEQ ID NO:1, wherein at least one addition, subtraction, or substitution is within positions 1 to 6 of SEQ ID NO: 1.

In another aspect, this document features a host cell containing a nucleic acid that encodes a natriuretic polypeptide having the amino acid sequence set forth in SEQ ID NO:1, with the proviso that the polypeptide includes one, two, three, four, or five amino acid additions, subtractions, or substitutions as compared to SEQ ID NO:1, wherein at least one addition, subtraction, or substitution is within positions 1 to 6 of SEQ ID NO:1. The host cell can be a eukaryotic host cell.

In yet another aspect, this document features a pharmaceutical composition containing a pharmaceutically acceptable carrier and a natriuretic polypeptide having the amino acid sequence set forth in SEQ ID NO:1, with the proviso that the polypeptide includes one, two, three, four, or five amino acid additions, subtractions, or substitutions as compared to SEQ ID NO:1, wherein at least one addition, subtraction, or substitution is within positions 1 to 6 of SEQ ID NO:1. The polypeptide can contain one to five conservative amino acid substitutions as compared to SEQ ID NO:1, or can contain one to three conservative amino acid substitutions as compared to SEQ ID NO:1. The polypeptide can contain one or two non-conservative amino acid substitutions as compared to SEQ ID NO:1. The serine at position 6 of SEQ ID NO:1 can be substituted with D-serine (SEQ ID NO:4). The arginine at position 4 of SEQ ID NO:1 can be substituted with D-arginine and the serine at position 5 of SEQ ID NO:1 can be deleted (SEQ ID NO:5). The polypeptide can contain the amino acid sequence set forth in SEQ ID NO:2, SEQ ID NO:3, SEQ ID NO:6, or SEQ ID NO:15.

In another aspect, this document features a method for increasing natriuretic activity within a mammal. The method can include administering to the mammal an effective amount of a composition that contains a natriuretic polypeptide having the amino acid sequence set forth in SEQ ID NO:1, with the proviso that the polypeptide includes one, two, three, four, or five amino acid additions, subtractions, or substitutions as compared to SEQ ID NO:1, wherein at least one addition, subtraction, or substitution is within positions 1 to 6 of SEQ ID NO:1. The polypeptide can include one to five conservative amino acid substitutions as compared to SEQ ID NO:1, or can include one to three conservative amino acid substitutions as compared to SEQ ID NO:1. The serine at position 6 of SEQ ID NO:1 can be substituted with D-serine (SEQ ID NO:4). The mammal can be a human. The composition can be administered at a dose of 0.01 ng/kg to 50 µg/kg. The method can include administering the composition intravenously. The method can further include identifying the mammal as being in need of increased natriuretic activity.

In still another aspect, this document features a method for treating a cardiovascular or metabolic disorder in a mammal in need thereof. The method can include administering to the mammal an effective amount of a composition containing a natriuretic polypeptide having the amino acid sequence set forth in SEQ ID NO:1, with the proviso that the polypeptide includes one, two, three, four, or five amino acid additions, subtractions, or substitutions as compared to SEQ ID NO:1, wherein at least one addition, subtraction, or substitution is within positions 1 to 6 of SEQ ID NO:1. The cardiovascular disorder can be hypertension, and the composition can be administered in an amount effective to reduce the blood pressure of the mammal. The polypeptide can include one to five conservative amino acid substitutions as compared to SEQ ID NO:1, or can include one to three conservative amino acid substitutions as compared to SEQ ID NO:1. The serine at position 6 of SEQ ID NO:1 can be substituted with D-serine (SEQ ID NO:4). The mammal can be a human. The composition can be administered at a dose of 0.01 ng/kg to 50 µg/kg. The method can include administering the composition intravenously. The method can further include identifying the mammal as being in need of the treatment.

This document also features the use of a natriuretic polypeptide in the manufacture of a medicament for treating a cardiovascular disorder, wherein the polypeptide has the amino acid sequence set forth in SEQ ID NO:1, with the proviso that the polypeptide comprises one, two, three, four, or five amino acid additions, subtractions, or substitutions as compared to SEQ ID NO:1, wherein at least one addition, subtraction, or substitution is within positions 1 to 6 of SEQ ID NO:1. The cardiovascular disorder can include hypertension. The polypeptide can include one to five conservative amino acid substitutions as compared to SEQ ID NO:1, or can include one to three conservative amino acid substitutions as compared to SEQ ID NO:1. The serine at position 6 of SEQ ID NO:1 can be substituted with D-serine (SEQ ID NO:4).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A-2E are a series of graphs plotting the effect of MANP, administered intravenously at the indicated doses, on mean arterial pressure (FIG. 2A), cGMP levels in plasma (FIG. 2B) and urine (FIG. 2C), distal tubule sodium reabsorption (FIG. 2D), and urinary sodium excretion (FIG. 2E) in spontaneously hypertensive rats.

FIG. 4 is a graph plotting cGMP levels as a measure of pGC-A receptor activation, expressed as a percent change from MANP. HEK293 cells overexpressing pGC-A were stimulated with the indicated MANP analogues; the sequences of the peptides tested are shown at the bottom of the figure.

FIG. 5A), heart rate (FIG. 5B), pulmonary wedge capillary pressure (PWCP; FIG. 5C), cardiac output (FIG. 5D), renal blood flow (FIG. 5E), urine output (UV; FIG. 5F), and urinary sodium excretion (UNaV; FIG. 5G) in a normal dog. After a baseline (BL) clearance, MANP18 was infused with saline for a total of 45 minutes, which included a 15-minute lead-in period followed by a 30-minute clearance. After the peptide infusion was discontinued, and four, 30-minute clearances were performed [washout (Wo), recovery 1 (Rec1), recovery 2 (Rec2), and recovery 3 (Rec3)].

FIG. 6F), and plasma angiotensin II levels (ANGII; FIG. 6G) in a normal dog. Experiments were conducted as described for FIGS. 5A-5G).

DETAILED DESCRIPTION

Figure 1:
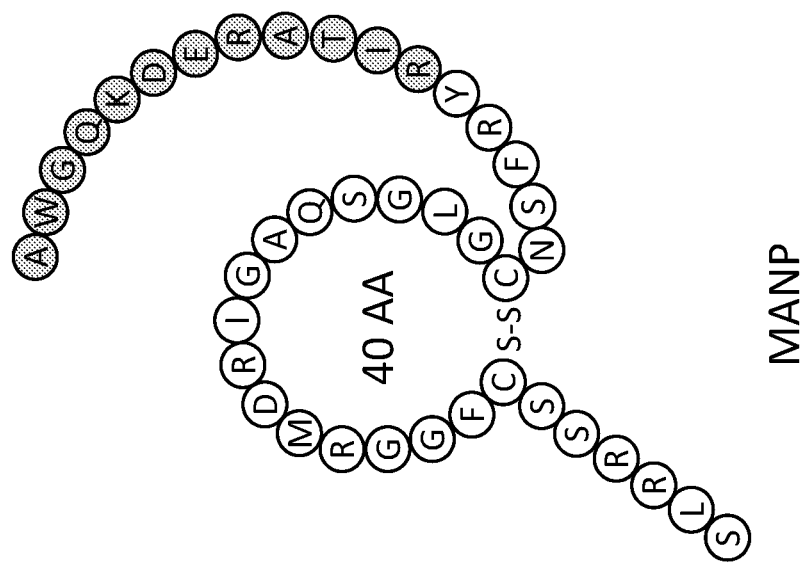
FIG. 1 shows the sequence of the MANP peptide (SEQ ID NO:1). MANP includes the 28 amino acid ANP sequence at its N-terminus, followed by a 12 amino acid, alternatively spliced tail at the C-terminus. Thus, MANP includes a six amino acid N-terminal portion (the first six amino acids of ANP), a 17 amino acid ring portion (the 17 amino acid ring of ANP), and a 17 amino acid C-terminal portion (the five C-terminal amino acids of ANP, followed by the 12 amino acid tail).

This disclosure provides methods and materials related to natriuretic polypeptides, and particularly to variants of MANP. For example, this document provides substantially pure variants of MANP having a natriuretic polypeptide activity, compositions containing such polypeptides, nucleic acid molecules encoding polypeptides having natriuretic polypeptide activity, and host cells containing isolated nucleic acid molecules that encode polypeptides having a natriuretic polypeptide activity. In addition, this document provides methods and materials for treating a cardiovascular or metabolic disorder in a mammal (e.g., a rodent, pig, sheep, dog, or human).

In some embodiments, natriuretic polypeptides can be effective to increase plasma cGMP levels, increase urinary cGMP excretion, increase net renal cGMP generation, increase urine flow, increase urinary sodium excretion, increase urinary potassium excretion, increase hematocrit, increase plasma BNP immunoreactivity, increase renal blood flow, increase plasma ANP immunoreactivity, decrease renal vascular resistance, decrease proximal and distal fractional reabsorption of sodium, decrease mean arterial pressure, decrease pulmonary wedge capillary pressure, decrease right atrial pressure, decrease pulmonary arterial pressure, decrease plasma renin activity, decrease plasma angiotensin II levels, decrease plasma aldosterone levels, decrease renal perfusion pressure, and/or decrease systemic vascular resistance.

The amino acid sequence for endogenous human mature ANP is SLRRSSCFGGRMDRIGAQSGLGCNSFRY (SEQ ID NO:7). Like other mature natriuretic polypeptides, ANP includes a 17-amino acid ring structure with a cysteine bond between the cysteine residues at positions 1 and 17 (underlined in the above sequence) of the ring.

The sequences of mature human BNP, CNP, and urodilatin are as follows:

```
BNP:
                                        (SEQ ID NO: 8)
SPKMVQGSGCFGRKMDRISSSSGLGCKVLRRH

CNP:
                                        (SEQ ID NO: 9)
GLSKGCFGLKLDRIGSMSGLGC

URO:
                                        (SEQ ID NO: 10)
TAPRSLRRSSCFGGRMDRIGAQSGLGCNSFRY
```

*Dendroaspis* natriuretic peptide (DNP), from the venom of *Dendroaspis angusticeps* (green mamba snake), has sequence and structural similarity to ANP, BNP, and CNP:

```
DNP:
                                        (SEQ ID NO: 11)
EVKYDPCFGHKIDRINHVSNLGCPSLRDPRPNAPSTSA.
```

The cysteine residues at the ends of the ring structures formed by the above sequences are underlined.

A natriuretic polypeptide can contain one or more sequences present in a polypeptide having natriuretic polypeptide activity (e.g., ANP, BNP, CNP, urodilatin, and DNP), but in some embodiments, a polypeptide having natriuretic polypeptide activity also can have a non-naturally occurring sequence or can include a sequence present in any species (e.g., human, horse, pig, goat, cow, dog, cat, rat, or mouse).

The term "isolated" as used herein with reference to a polypeptide means that the polypeptide (1) is not associated with proteins found in nature, (2) is free of other proteins from the same source (e.g., free of human proteins), (3) is expressed by a cell from a different species, or (4) does not occur in nature. An isolated polypeptide can be, for example, encoded by DNA or RNA, including synthetic DNA or RNA, or some combination thereof.

The term "substantially pure" as used herein with reference to a polypeptide means the polypeptide is substantially free of other polypeptides, lipids, carbohydrates, and nucleic acid with which it is naturally associated. A substantially pure polypeptide can be any polypeptide that is removed from its natural environment and is at least 60 percent pure. A substantially pure polypeptide can be at least about 65, 70, 75, 80, 85, 90, 95, or 99 percent pure, or about 65 to 75, 75 to 80, 80 to 85, 85 to 90, 90 to 95, or 95 to 99 percent pure. Typically, a substantially pure polypeptide will yield a single major band on a non-reducing polyacrylamide gel. In some embodiments, a substantially pure polypeptide can be a chemically synthesized polypeptide.

Any method can be used to obtain a substantially pure polypeptide. For example, polypeptide purification techniques, such as affinity chromatography and HPLC, as well as polypeptide synthesis techniques can be used. In addition, any material can be used as a source to obtain a substantially pure polypeptide. For example, tissue from wild-type or transgenic animals can be used as a source material. In addition, tissue culture cells engineered to over-express a particular polypeptide can be used to obtain substantially pure polypeptide. Further, a polypeptide can be engineered to contain an amino acid sequence that allows the polypeptide to be captured onto an affinity matrix. For example, a tag such as c-myc, hemagglutinin, polyhistidine, or FLAG™ tag (Kodak) can be used to aid polypeptide purification. Such tags can be inserted anywhere within the polypeptide including at either the carboxyl or amino termini, or in between. Other fusions that can be used include enzymes that aid in the detection of the polypeptide, such as alkaline phosphatase.

A polypeptide having natriuretic activity can be a variant of an MANP polypeptide. MANP is an ANP-based peptide having an amino acid sequence that includes the 28 amino acid mature human ANP sequence (SLRRSSCFGGRMDRI-GAQSGLGCNSFRY; SEQ ID NO:7) with an additional 12 amino acid carboxy terminus (RITAREDKQGWA; SEQ ID NO:12). The full length sequence of MANP is SLRRSS-CFGGRMDRIGAQSGLGCNSFRYRITAREDKQGWA (SEQ ID NO:1). The nucleic acid sequence 5'-agcctgcg-gagatccagctgcttcggggggcaggatg gacaggattg-gagcccagagcggactgggctgtaacagcttccggtaccgaagataa-3' (SEQ ID NO:13) is a representative sequence that encodes human ANP, and the nucleic acid sequence 5'-agcctgcg-gagatccagctgcttcggggggcaggatggacaggattg-gagcccagagcggactgggctgtaacagatcc ggtaccggataacagccagg-gaggacaagcagggctgggcctag-3' (SEQ ID NO:14) is a representative sequence that encodes MANP.

MANP (SEQ ID NO:1) has greater diuretic and natriuretic effects than ANP (SEQ ID NO:7) in normal dogs; low dose MANP also has a greater effect than low dose ANP on renal blood flow. See, U.S. Pat. Nos. 7,803,901 and 8,063,191, both of which are incorporated herein by reference in their entirety. No change in glomerular filtration rate (GFR) or mean arterial pressure (MAP) was observed during infusion of a low dose of MANP or ANP, whereas infusion of a high dose of MANP increased GFR and decreased MAP as compared to the effects of a high dose of ANP.

The polypeptides provided herein can contain the entire amino acid sequence set forth in SEQ ID NO:1, except that the amino acid sequence can contain from one to ten (e.g., ten, one to nine, two to nine, one to eight, two to eight, one to seven, one to six, one to five, one to four, one to three, two, or one) amino acid additions, subtractions, and substitutions, or modifications. For example, a polypeptide can contain the amino acid sequence set forth in SEQ ID NO:1 with one, two, three, four, five, six, seven, eight, nine, or ten single amino acid residue additions, subtractions, or substitutions. Variant polypeptides containing additions, subtractions, and/or substitutions within the N-terminal portion of SEQ ID NO:1 (the first six amino acids of SEQ ID NO:1) may be particularly useful. Examples of such polypeptides include, without limitation, a polypeptide having the amino acid sequence set forth in SEQ ID NO:1 where four amino acids from urodilatin are added to the N-terminus (SEQ ID NO:2), the arginine residues at positions 3 and 4 are substituted with lysine residues (SEQ ID NO:3), the D-isoform of serine is substituted at the sixth position (SEQ ID NO:4), the D-isoform of arginine is substituted at the fourth position and the serine at the fifth position is deleted (SEQ ID NO:5), threonine residues are substituted for the serines at positions 1, 5, and 6 (SEQ ID NO:6), a tryptophan is substituted for the leucine at position 2 (SEQ ID NO:15), or any combination thereof.

Any amino acid residue set forth in SEQ ID NO:1 can be subtracted, and any amino acid residue (e.g., any of the 20 conventional amino acid residues or any other type of amino acid such as ornithine or citrulline) can be added to or substituted within the sequence set forth in SEQ ID NO:1. The majority of naturally occurring amino acids are L-amino acids, and naturally occurring polypeptides are largely comprised of L-amino acids. D-amino acids are the enantiomers of L-amino acids. In some cases, a polypeptide as provided herein can contain one or more D-amino acids (e.g., D-serine or D-arginine as in SEQ ID NOS:4 and 5, or at any other position or positions within SEQ ID NO:1). In some embodiments, a polypeptide can contain chemical structures such as ε-aminohexanoic acid; hydroxylated amino acids such as 3-hydroxyproline, 4-hydroxyproline, (5R)-5-hydroxy-L-lysine, allo-hydroxylysine, and 5-hydroxy-L-norvaline; or glycosylated amino acids such as amino acids containing monosaccharides (e.g., D-glucose, D-galactose, D-mannose, D-glucosamine, and D-galactosamine) or combinations of monosaccharides.

Natriuretic polypeptides having one or more amino acid additions, subtractions, or substitutions relative to a native natriuretic polypeptide amino acid sequence (also referred to herein as "variant" natriuretic polypeptides) can be prepared and modified as described herein. In some cases, amino acid substitutions can be made by selecting substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of useful conservative substitutions can include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine.

Further examples of conservative substitutions that can be made at any position within the polypeptides provided herein are set forth in TABLE 1.

TABLE 1

Examples of conservative amino acid substitutions

| Original Residue | Exemplary substitutions | Preferred substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleucine | Leu |

In some embodiments, a natriuretic polypeptide can include one or more non-conservative substitutions. Non-conservative substitutions typically entail exchanging a member of one of the classes described above for a member of another class. Such production can be desirable to provide large quantities or alternative embodiments of such compounds. Whether an amino acid change results in a functional polypeptide can readily be determined by assaying the specific activity of the peptide variant using, for example, methods disclosed herein.

In some embodiments, a polypeptide as provided herein can have a length of, for example, 35 to 45 amino acid residues (e.g., 35 to 40, 40 to 45, 35 to 37, 36 to 38, 37 to 39, 38 to 40, 39 to 41, 40 to 42, 41 to 43, 42 to 44, or 43 to 45 amino acid residues).

In some embodiments, a natriuretic polypeptide can comprise an amino acid sequence as set forth in SEQ ID NO:1, but with a particular number of amino acid substitutions. For example, a natriuretic polypeptide can have the amino acid sequence of SEQ ID NO:1, but with one, two, three, four, or five amino acid substitutions. Examples of such amino acid sequences include, without limitation, MANP with a D-amino acid replacing one or more L-amino acids within the N-terminal region of the polypeptide (e.g., with a D-serine residue at position 6, as set forth in SEQ ID NO:4, or with a D-arginine at position 4, as set forth in SEQ ID NO:5).

In some embodiments, a natriuretic polypeptide as provided herein can include an amino acid sequence with at least 85% (e.g., 85%, 86%, 87%, 88%, 89%, 90%, 91%, 92%, 93%, 94%, 95%, 96%, 97%, 97.5%, 98%, 98.5%, 99.0%, 99.5%, 99.6%, 99.7%, 99.8%, 99.9%, or 100%) sequence identity to a region of a reference natriuretic polypeptide sequence (e.g., SEQ ID NO:1). Percent sequence identity is calculated by determining the number of matched positions in aligned amino acid sequences, dividing the number of matched positions by the total number of aligned amino acids, and multiplying by 100. A matched position refers to a position in which identical amino acids occur at the same position in aligned amino acid sequences. Percent sequence identity also can be determined for any nucleic acid sequence.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\Bl2seq c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 20 consecutive nucleotides or amino acid residues from a sequence set forth in an identified sequence), followed by multiplying the resulting value by 100. For example, an amino acid sequence that has 37 matches when aligned with the sequence set forth in SEQ ID NO:1 is 92.5 percent identical to the sequence set forth in SEQ ID NO:1 (i.e., 37÷40×100=92.5). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

Isolated polypeptides can be produced using any suitable methods, including solid phase synthesis, and can be generated using manual techniques or automated techniques (e.g., using an Applied BioSystems (Foster City, Calif.) Peptide Synthesizer or a Biosearch Inc. (San Rafael, Calif.) automatic peptide synthesizer). Disulfide bonds between cysteine residues can be introduced by mild oxidation of the linear polypeptides using KCN as taught, e.g., in U.S. Patent No. 4,757,048. Natriuretic polypeptides also can be produced recombinantly, or obtained commercially.

The natriuretic polypeptides provided herein typically are cyclic due to disulfide bonds between the cysteine residues underlined in the sequences shown above. In some embodiments, a sulfhydryl group on a cysteine residue can be replaced with an alternative group (e.g., —$CH_2CH_2$—). To replace a sulfhydryl group with a —$CH_2$— group, for example, a cysteine residue can be replaced by alpha-aminobutyric acid. Such cyclic analog polypeptides can be generated, for example, in accordance with the methodology of Lebl and Hruby ((1984) *Tetrahedron Lett.* 25:2067-2068), or by employing the procedure disclosed in U.S. Pat. No. 4,161,521.

In addition, ester bridges can be formed by reacting the OH of serine or threonine with the carboxyl group of aspartic acid or glutamic acid to yield a bridge having the structure —$CH_2CO_2CH_2$—. Similarly, an amide can be obtained by reacting the side chain of lysine with aspartic acid or glutamic acid to yield a bridge having the structure —$CH_2C(O)NH(CH)_4$—. Methods for synthesis of these bridges are known in the art (see, e.g., Schiller et al. (1985) *Biochem. Biophys. Res. Comm.* 127:558, and Schiller et al. (1985) *Int. J. Peptide Protein Res.* 25:171). For example, one method for preparing esters of the present polypeptides, when using the Merrifield synthesis technique, is to cleave the completed polypeptide from the resin in the presence of the desired alcohol under either basic or acidic conditions, depending upon the resin. The C-terminal end of the polypeptide then can be directly esterified when freed from the resin, without isolation of the free acid. Amides of polypeptides also can be prepared using techniques (e.g., those known in the art) for converting a carboxylic acid group or precursor to an amide. One method for amide formation at the C-terminal carboxyl group includes cleaving the polypeptide from a solid support with an appropriate amine, or cleaving in the presence of an alcohol, yielding an ester, followed by aminolysis with the desired amine. Other bridge-forming amino acid residues and reactions are provided in, for example, U.S. Pat. No. 4,935,492. Preparation of peptide analogs that include non-peptidyl bonds to link amino acid residues also are known in the art. See, e.g., Spatola et al. (1986) *Life Sci.* 38:1243; Spatola (1983) *Vega Data* 1(3); Morley (1980) *Trends Pharm. Sci.* 463-468; Hudson et al. (1979) Int. Pept. Prot. Res. 14:177; Spatola, in *Chemistry and Biochemistry of Amino Acid Peptides and Proteins,* B. Weinstein, ed., Marcel Dekker, New York, p. 267 (1983); Hann (1982) *J Chem. Soc. Perkin Trans.* 1:307; Almquist et al. (1980) *J Med. Chem.* 23:1392; Jennings-White et al. (1982) *Tetrahedron Lett.* 23:2533; European Patent Application EP 45665; Holladay et al. (1983) *Tetrahedron Lett.* 24:4401; and Hruby (1982) Life Sci. 31:189.

N-acyl derivatives of an amino group of a polypeptide can be prepared by utilizing an N-acyl protected amino acid for the final condensation, or by acylating a protected or unprotected peptide. O-acyl derivatives can be prepared for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

In some cases, a polypeptide provided herein can be pegylated, acetylated, or both. In some cases, a polypeptide provided herein can be covalently attached to oligomers, such as short, amphiphilic oligomers that enable administration or improve the pharmacokinetic or pharmacodynamic profile of the conjugated polypeptide. The oligomers can comprise water soluble polyethylene glycol (PEG) and/or lipid soluble alkyls (short, medium, or long chain fatty acid polymers, such as, without limitation, palmitic acid, myristic acid, lauric acid, capric acid, or steric acid). The fatty acid molecule can be attached to the free amino terminus or to any lysine side chain (an epsilon amino group), and a lysine residue for this attachment can be placed at either the C-terminal or N-terminal end of the peptide. Linkage to PEG or another suitable polymer, or fusion to albumin or another suitable polypeptide can result in a modified natriuretic polypeptide having an increased half-life as compared to an unmodified natriuretic polypeptide. Without being bound by a particular mechanism, an increased serum half-life can result from reduced proteolytic degradation, immune recognition, or cell scavenging of the modified natriuretic polypeptide. Methods for modifying a polypeptide by linkage to PEG (also referred to as "PEGylation") or other polymers are known in the art, and include those set forth in U.S. Pat. No. 6,884,780; PCT Publication No. WO 2004/047871; Cataliotti et al. ((2007) *Trends Cardiovasc. Med.* 17:10-14; Veronese and Mero (2008) *BioDrugs* 22:315-329; Miller et al. (2006) *Bioconjugate Chem.* 17:267-274; and Veronese and Pasut (2005) *Drug Discov. Today* 10:1451-1458, all of which are incorporated herein by reference in their entirety. Methods for modifying a polypeptide by fusion to albumin also are known in the art, and include those set forth in U.S. Patent Publication No. 20040086976, and Wang et al. (2004) *Pharm. Res.* 21:2105-2111, both of which are incorporated herein by reference in their entirety.

In some cases, a polypeptide provided herein can be fused to the Fc domain of an immunoglobulin molecule (e.g., an IgG1 molecule) such that active transport of the fusion polypeptide across epithelial cell barriers occurs via the Fc receptor. In some cases, a polypeptide can be a cyclic polypeptide. A cyclic polypeptide provided herein can be obtained by bonding cysteine residues. However, the replacement of a sulfhydryl group on the cysteine residue with an alternative group (e.g., —$CH_2$—$CH_2$—) also is envisioned, for example, To replace sulfhydryl groups with a —$CH_2$— group, the cysteine residues can be replaced by the analogous alpha-aminobutyric acid. These cyclic analog peptides can be formed, for example, in accordance with the methodology of Lebl and Hruby (supra), or by employing the procedure disclosed in U.S. Pat. No. 4,161,521.

Salts of carboxyl groups of polypeptides can be prepared by contacting a polypeptide with one or more equivalents of a desired base such as, for example, a metallic hydroxide base (e.g., sodium hydroxide), a metal carbonate or bicarbonate base (e.g., sodium carbonate or sodium bicarbonate), or an amine base (e.g., triethylamine, triethanolamine, and the like). Acid addition salts of polypeptides can be prepared by contacting the polypeptide with one or more equivalents of an inorganic or organic acid (e.g., hydrochloric acid).

The natriuretic polypeptides provided herein can function through one or more of the guanylyl cyclase receptors through which the native natriuretic polypeptides function. For example, the polypeptides provided herein typically bind to and function through the NPR-A receptor through which ANP and BNP function, although they also may function through the NPR-B receptor through which CNP functions. Further, in some cases, a natriuretic polypeptide as provided herein can bind to and function through more than one guanylyl cyclase receptor, including NPR-A and NPR-B, for example. Methods for evaluating which receptor is involved in function of a particular natriuretic polypeptide are known in the art. For example, glomeruli, which contain both NPR-A and NPR-B, can be isolated (e.g., from a laboratory animal such as a dog) and incubated with a natriuretic polypeptide (e.g., a native or mutated natriuretic polypeptide), and cGMP levels can be measured. Glomeruli can be pretreated with antagonists of NPR-A or NPR-B to determine whether cGMP production stimulated by a natriuretic polypeptide through one or the other receptor can be attenuated.

In some cases, an isolated natriuretic polypeptide and herein can be used to treat cardiovascular, metabolic, or cardiorenal disease. For example, the polypeptides provided herein can be used to treat hypertension or heart failure. The presence or extent of disease can be evaluated using methods known in the art, including, without limitation, general clinical examination to evaluate blood pressure, heart rate, heart rhythm, arterial oxygen, and hemoglobin levels; echocardiography to measure ejection fraction, LV and left atrium (LA) diameter, LV wall motion, LV filling pressure, and diastolic function by pulse and tissue Doppler; use of a Swan-Ganz catheter to measure cardiac output, pulmonary wedge capillary pressure, pulmonary arterial pressure, right ventricle pressure, right atrium pressure, and systemic and pulmonary vascular resistance; assessment of kidney function by determination of glomerular filtration rate, serum creatinine, and blood urea nitrogen; and measurement of biomarkers such as BNP, amino-terminal proBNP (NT-proBNP), troponin-T, troponin-I, C-reactive protein (CRP), and creatine-kinase, serum cystatin-C, albuminuria, neutrophil gelatinize associated lopocalin (NGAL), N-acetyl-beta-D-glucosaminidase (NAG), kidney injury molecule-1 (KIM-1), angiotensin-II, renin, aldosterone, and inflammatory cytokines (e.g., interleukin (IL)-6, IL-18, etc.). In some cases, an isolated natriuretic polypeptide as provided herein can reduce one or more symptoms of acute HF, including clinical parameters such as edema, shortness of breath, and fatigue, as well as cardiac unloading (i.e., reduced pressure in the heart), increased glomerular filtration rate (GFR), decreased PRA, decreased levels of angiotensin II, decreased proliferation of cardiac fibroblasts, decreased left ventricular (LV) hypertrophy, decreased LV mass (indicative of reduced fibrosis and hypertrophy), decreased PWCP (an indirect measure of left atrial pressure), decreased right atrial pressure, decreased mean arterial pressure, decreased levels of aldosterone (indicative of an anti-fibrotic effect), decreased ventricular fibrosis, increased ejection fraction, and decreased LV end systolic diameter. To determine whether a natriuretic polypeptide is capable of inhibiting or reducing a symptom of acute HF, one or more of these parameters can be evaluated (e.g., before and after treatment with the natriuretic polypeptide), using methods known in the art, for example.

Variant natriuretic polypeptides having conservative and/or non-conservative substitutions with respect to SEQ ID NO:1 (e.g., polypeptides comprising any of SEQ ID NOS: 2-6 and 15), as well as fragments of variants of SEQ ID NO:1 (e.g., fragments of any of SEQ ID NOS:2-6 and 15), can be screened for biological activity using any of a number of assays, including those described herein. For example, the activity of a natriuretic polypeptide as described herein can be evaluated in vitro by testing its effect on cGMP production in cultured cells (e.g., cultured cardiac fibroblasts, aortic endothelial cells, or glomerular cells). Cells can be exposed to a natriuretic polypeptide (e.g., $10^{-10}$ to $10^{-4}$ M natriuretic polypeptide), and samples can be assayed to evaluate the natriuretic polypeptide's effects on cGMP generation. cGMP generation can be detected and measured using, for example, a competitive RIA cGMP kit (Perkin-Elmer, Boston, Mass.).

The activity of a natriuretic polypeptide also can be evaluated in vivo by, for example, testing its effects on factors such as plasma cGMP levels, urinary cGMP excretion, net renal generation of cGMP, glomerular filtration rate, blood pressure, heart rate, hemodynamic function such as cardiac output, pulmonary wedge pressure, systemic vascular resistance, and renal function such as renal blood flow, urine volume, and sodium excretion rate in a mammal (e.g., a rodent, pig, sheep, dog, or human). In some cases, such parameters can be evaluated after inducing heart failure (e.g., by rapid right ventricular pacing) or hypertension.

This document also provides nucleic acid molecules encoding the polypeptides provided herein. For example, this document provides nucleic acid molecules encoding natriuretic peptides that are variants of the polypeptide having the amino acid sequence set forth in SEQ ID NO:1 (e.g., any of SEQ ID NOS:2-6 and 15, or variants of SEQ ID NOS:2-6 and 15, or other variants of SEQ ID NO:1 (particularly within the N-terminal portion) that differ from SEQ ID NOS:2-6 and 15. Thus, a nucleic acid molecule as provided herein can encode a polypeptide that contains the amino acid sequence set forth in SEQ ID NO:1, except that the amino acid sequence contains one to ten (e.g., one to nine, two to nine, one to eight, two to eight, one to seven, one to six, one to five, one to four, one to three, two, or one) amino acid additions, subtractions, and substitutions as described herein, typically where at least one (e.g., one, two, three, or four) of the amino acid additions, subtractions, or substitutions are with respect to the N-terminal portion of SEQ ID NO:1.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

In some cases, an isolated nucleic acid molecule provided herein can be at least about 12 bases in length (e.g., at least about 13, 14, 15, 16, 17, 18, 19, 20, 25, 30, 40, 50, 60, 100, 120, 130, 140, 150, 250, 500, 750, 1000, 1500, 2000, 3000, 4000, or 5000 bases in length) and hybridize, under hybridization conditions, to the sense or antisense strand of a nucleic acid having a sequence that encodes a variant of the sequence set forth in SEQ ID NO:1. The hybridization conditions can be moderately or highly stringent hybridization conditions. In some cases, such nucleic acid molecules can be molecules that do not hybridize to the sense or antisense strand of a nucleic acid that consists only of the coding sequence of a natriuretic peptide such as human ANP or human MANP.

For the purpose of this document, moderately stringent hybridization conditions mean the hybridization is performed at about 42° C. in a hybridization solution containing 25 mM $KPO_4$ (pH 7.4), 5× SSC, 5× Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 50° C. with a wash solution containing 2× SSC and 0.1% sodium dodecyl sulfate.

Highly stringent hybridization conditions mean the hybridization is performed at about 42° C. in a hybridization solution containing 25 mM $KPO_4$ (pH 7.4), 5× SSC, 5× Denhart's solution, 50 µg/mL denatured, sonicated salmon sperm DNA, 50% formamide, 10% Dextran sulfate, and 1-15 ng/mL probe (about $5 \times 10^7$ cpm/m), while the washes are performed at about 65° C. with a wash solution containing 0.2× SSC and 0.1% sodium dodecyl sulfate.

Isolated nucleic acid molecules can be produced using standard techniques, including, without limitation, common molecular cloning and chemical nucleic acid synthesis techniques. For example, polymerase chain reaction (PCR) techniques can be used to obtain an isolated nucleic acid containing nucleotide sequence that encodes a natriuretic polypeptide as provided herein. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual,* ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids (e.g., nucleic acids encoding variant natriuretic polypeptides) also can be obtained by mutagenesis. For example, a reference sequence can be mutated using standard techniques including oligonucleotide-directed mutagenesis and site-directed mutagenesis through PCR. See, *Short Protocols in Molecular Biology,* Chapter 8, Green Publishing Associates and John Wiley & Sons, edited by Ausubel et al., 1992. Non-limiting examples of variant natriuretic polypeptides are provided herein.

Vectors containing nucleic acids such as those described herein also are provided. A "vector" is a replicon, such as a plasmid, phage, or cosmid, into which another DNA segment may be inserted so as to bring about the replication of the inserted segment. An "expression vector" is a vector that includes one or more expression control sequences, and an "expression control sequence" is a DNA sequence that controls and regulates the transcription and/or translation of another DNA sequence.

In an expression vector, a nucleic acid (e.g., a nucleic acid encoding a natriuretic polypeptide) can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 to 500 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence. Expression vectors thus can be useful to produce antibodies as well as other multivalent molecules.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

Host cells containing vectors also are provided. The term "host cell" is intended to include prokaryotic and eukaryotic cells into which a recombinant expression vector can be introduced (e.g., vector encoding a polypeptide containing a variant of the amino acid sequence set forth in SEQ ID NO:1). As used herein, "transformed" and "transfected" encompass the introduction of a nucleic acid molecule (e.g., a vector) into a cell by one of a number of techniques. Although not limited to a particular technique, a number of these techniques are well established within the art. Suitable methods for transforming and transfecting host cells can be found, for example, in Sambrook et al., Molecular Cloning: A Laboratory Manual ($2^{nd}$ edition), Cold Spring Harbor Laboratory, New York (1989). For example, calcium phosphate precipitation, electroporation, heat shock, lipofection, microinjection, and viral-mediated nucleic acid transfer can be used introduce nucleic acid into cells. In addition, naked DNA can be delivered directly to cells in vivo as described elsewhere (U.S. Pat. Nos. 5,580,859 and 5,589,466). The host cells can express the encoded polypeptide, but it is noted that cells containing an isolated nucleic acid molecule provided herein are not required to express a polypeptide. The isolated nucleic acid molecule transformed into a host cell can be integrated into the genome of the cell or maintained in an episomal state. Thus, host cells can be stably or transiently transfected with a construct containing an isolated nucleic acid molecule provided herein.

Any suitable method can be used to introduce an isolated nucleic acid molecule into a cell in vivo or in vitro, including methods known in the art. For example, calcium phosphate precipitation, electroporation, heat shock, lipofection, microinjection, and viral-mediated nucleic acid transfer are methods that can be used to introduce an isolated nucleic acid molecule into a cell. In addition, naked DNA can be delivered directly to cells in vivo as described elsewhere (e.g., U.S. Pat. Nos. 5,580,859 and 5,589,466, and continuations thereof). Further, isolated nucleic acid molecules can be introduced into cells by generating transgenic animals.

Any suitable method, including methods known in the art, can be used to identify cells containing an isolated nucleic acid molecule provided herein. Such methods include, without limitation, PCR and nucleic acid hybridization techniques such as Northern and Southern analyses. In some cases, immunohistochemistry and biochemical techniques can be used to determine if a cell contains a particular isolated nucleic acid molecule by detecting the expression of a polypeptide encoded by that nucleic acid molecule.

The natriuretic polypeptides described herein (e.g., variants of MANP), or nucleic acids encoding the natriuretic polypeptides described herein, can be incorporated into compositions for administration to a subject (e.g., a subject suffering from or at risk for hypertension and/or cardiorenal disease). Methods for formulating and subsequently administering therapeutic compositions are well known to those in the art. Dosages typically are dependent on the responsiveness of the subject to the compound, with the course of treatment lasting from several days to several months, or until a suitable response is achieved. Persons of ordinary skill in the art routinely determine optimum dosages, dosing methodologies and repetition rates. Optimum dosages can vary depending on the relative potency of an antibody, and generally can be estimated based on the $EC_{50}$ found to be effective in in vitro and/or in vivo animal models. Compositions containing the compounds (e.g., natriuretic polypeptides) and nucleic acids provided herein may be given once or more daily, weekly, monthly, or even less often, or can be administered continuously for a period of time (e.g., hours, days, or weeks). For example, a natriuretic polypeptide or a composition containing a natriuretic polypeptide can be administered to a patient at a dose of at least about 0.01 ng natriuretic polypeptide/kg to about 100 mg natriuretic polypeptide/kg of body mass at or about the time of reperfusion, or can be administered continuously as an infusion beginning at or about the time of reperfusion and continuing for one to seven days (e.g., at a dose of about 0.01 ng natriuretic polypeptide/kg/minute to about 0.5 µg natriuretic polypeptide/kg/minute).

The natriuretic polypeptides and nucleic acids can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption.

In some embodiments, a composition can contain a natriuretic polypeptide as provided herein in combination with a pharmaceutically acceptable carrier. Pharmaceutically acceptable carriers include, for example, pharmaceutically acceptable solvents, suspending agents, or any other pharmacologically inert vehicles for delivering antibodies to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water; saline solution; binding agents (e.g., polyvinylpyrrolidone or hydroxypropyl methylcellulose); fillers (e.g., lactose or dextrose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions containing molecules described herein can be administered by a number of methods, depending upon whether local or systemic treatment is desired. Administration can be, for example, parenteral (e.g., by subcutaneous, intrathecal, intraventricular, intramuscular, or intraperitoneal injection, or by intravenous (i.v.) drip); oral; topical (e.g., transdermal, sublingual, ophthalmic, or intranasal); or pulmonary (e.g., by inhalation or insufflation of powders or aerosols), or can occur by a combination of such methods. Administration can be rapid (e.g., by injection) or can occur over a period of time (e.g., by slow infusion or administration of slow release formulations).

Compositions and formulations for parenteral, intrathecal or intraventricular administration include sterile aqueous solutions (e.g., sterile physiological saline), which also can contain buffers, diluents and other suitable additives (e.g., penetration enhancers, carrier compounds and other pharmaceutically acceptable carriers).

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Formulations for topical administration include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be useful. In some embodiments, transdermal delivery of natriuretic polypeptides as provided herein can be particularly useful. Methods and compositions for transdermal delivery include those described in the art (e.g., in Wermeling et al. (2008) *Proc. Natl. Acad. Sci. USA* 105:2058-2063; Goebel and Neubert (2008) *Skin Pharmacol. Physiol.* 21:3-9; Banga (2007) *Pharm. Res.* 24:1357-1359; Malik et al. (2007) *Curr. Drug Deliv.* 4:141-151; and Prausnitz (2006) *Nat. Biotechnol.* 24:416-417).

Nasal preparations can be presented in a liquid form or as a dry product. Nebulized aqueous suspensions or solutions can include carriers or excipients to adjust pH and/or tonicity.

Pharmaceutical compositions include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsion formulations are particularly useful for oral delivery of therapeutic compositions due to their ease of formulation and efficacy of solubilization, absorption, and bioavailability. Liposomes can be particularly useful due to their specificity and the duration of action they offer from the standpoint of drug delivery.

Compositions provided herein can contain any pharmaceutically acceptable salts, esters, or salts of such esters, or any other compound which, upon administration to a subject, is capable of providing (directly or indirectly) the biologically active metabolite or residue thereof for the relevant compound (e.g., natriuretic polypeptide). Accordingly, for example, this document provides pharmaceutically acceptable salts of natriuretic polypeptides, prodrugs and pharmaceutically acceptable salts of such prodrugs, and other bioequivalents. A prodrug is a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the natriuretic polypeptides useful in methods provided herein (i.e., salts that retain the desired biological activity of the parent natriuretic polypeptides without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); salts formed with organic acids (e.g., acetic acid, citric acid, oxalic acid, palmitic acid, or fumaric acid); and salts formed with elemental anions (e.g., bromine, iodine, or chlorine).

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions, such as dyes, flavoring agents, preservatives, antioxidants, opacifiers, thickening agents, and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, penetration enhancers, and aromatic substances. When added, however, such materials should not unduly interfere with the biological activities of the other components within the compositions.

In some cases, a polypeptide provided herein can be formulated as a sustained release dosage form. For example, a natriuretic polypeptide can be formulated into a controlled release formulation. In some cases, coatings, envelopes, or protective matrices can be formulated to contain one or more of the polypeptides provided herein. Such coatings, envelopes, and protective matrices can be used to coat indwelling devices such as stents, catheters, and peritoneal dialysis tubing. In some cases, a polypeptide provided herein can incorporated into a polymeric substances, liposomes, microemulsions, microparticles, nanoparticles, or waxes.

Pharmaceutical formulations as disclosed herein, which can be presented conveniently in unit dosage form, can be prepared according to conventional techniques well known in the pharmaceutical industry. Such techniques include the step of bringing into association the active ingredients (i.e., the antibodies) with the desired pharmaceutical carrier(s). Typically, the formulations can be prepared by uniformly and intimately bringing the active ingredients into association with liquid carriers or finely divided solid carriers or both, and then, if necessary, shaping the product. Formulations can be sterilized if desired, provided that the method of sterilization does not interfere with the effectiveness of the molecules(s) contained in the formulation.

In some embodiments, a natriuretic polypeptide provided herein can be formulated for subcutaneous delivery via depot polymers, drug patch, injection, pump, or microparticle/nano particle. Examples of such delivery methods are known in the art.

By way of example and not limitation, PCT Publication No. WO 2008/061355 discloses materials and methods for formulating a polypeptide for delivery in a hydrogel tube. The polypeptide can be mixed with one or more excipients that are pharmaceutically acceptable and are compatible with the polypeptide in amounts suitable for use in the methods described herein. For example, a polypeptide can be combined with one or more excipients such as, without limitation, microcrystalline cellulose, colloidal silicon dioxide, lactose, starch, sorbitol, cyclodextrin, and combinations thereof. The excipient can be a solid, semi-solid, or liquid material that acts as a vehicle, carrier, or medium for the polypeptide. In some embodiments, the polypeptide can be compressed, compacted, or extruded with one or more excipients prior to inserting it into a hydrogel tube. Such formulations can result in a pharmaceutical composition with desirable release properties, improved stability, and/or other desirable properties.

Pharmaceutical compositions also can include auxiliary agents or excipients, such as glidants, dissolution agents, surfactants, diluents, binders, disintegrants, and/or lubricants. For example, dissolution agents can increase the dissolution rate of the polypeptide from the dosage formulation, and can include, for example, organic acids and/or salts of organic acids (e.g., sodium citrate with citric acid). Other examples of excipients useful in such formulations include synthetic, semi-synthetic, modified, and natural polymers (e.g., lactose, dextrose, sucrose, trehalose, sorbitol, mannitol, starches, gum acacia, calcium silicate, microcrystalline cellulose, polyvinylpyrrolidone, cellulose, water, syrup, PEG, cyclodextrin, alkoxy-modified cyclodextrins, hydroxyethylcellulose, hydroxypropylcellulose, microcrystalline cellulose, albumin, dextran, malitol, xylitol, kaolin, and methyl cellulose). The polypeptide also can be mixed with a lubricating agent (e.g., talc, magnesium stearate, stearic acid, or mineral oil, calcium stearate, hydrogenated vegetable oils, sodium benzoate, sodium chloride, leucine carbowax, magnesium lauryl sulfate, or glyceryl monostearate), a wetting agent, an emulsifying and suspending agent, or a preserving agent (e.g., methyl or propyl hydroxybenzoate).

Other agents that can be added to a pharmaceutical composition can alter the pH of the microenvironment on dissolution and establishment of a therapeutically effective plasma concentration profile of the polypeptide. Such agents include salts of inorganic acids and magnesium hydroxide. Other agents that can be used include surfactants and other solubilizing materials.

Useful diluents include, for example, pharmaceutically acceptable inert fillers such as microcrystalline cellulose, lactose, sucrose, fructose, glucose dextrose, or other sugars, dibasic calcium phosphate, calcium sulfate, cellulose, ethylcellulose, cellulose derivatives, kaolin, mannitol, lactitol, maltitol, xylitol, sorbitol, or other sugar alcohols, dry starch, saccharides, dextrin, maltodextrin or other polysaccharides, inositol or combinations thereof. Water-soluble diluents can be particularly useful.

Glidants can be used to improve the flow and compressibility of composition ingredients during processing. Useful glidants include, for example, colloidal silicon dioxide (also referred to as colloidal silica, fumed silica, light anhydrous silicic acid, silicic anhydride, and silicon dioxide fumed).

Surfactants that are suitable for use in the pharmaceutical compositions provided herein include, without limitation, sodium lauryl sulphate, polyethylene stearates, polyethylene sorbitan fatty acid esters, polyoxyethylene castor oil derivatives, polyoxyethylene alkyl ethers, benzyl benzoate, cetrimide, cetyl alcohol, docusate sodium, glyceryl monooleate, glyceryl monostearate, glyceryl palmitostearate, lecithin, medium chain triglycerides, monoethanolamine, oleic acid, poloxarners, polyvinyl alcohol and sorbitan fatty acid esters.

Suitable disintegrants include, for example, starches, sodium starch glycolate, crospovidone, croscarmellose, microcrystalline cellulose, low substituted hydroxypropyl cellulose, pectins, potassium methacrylate-divinylbenzene copolymer, polyvinyl alcohol), thylamide, sodium bicarbonate, sodium carbonate, starch derivatives, dextrin, beta cyclodextrin, dextrin derivatives, magnesium oxide, clays, bentonite, and combinations thereof.

In some embodiments, a natriuretic polypeptide can be incorporated into a hydrogel delivery system. For example, a polypeptide can be formulated for subcutaneous delivery to a patient via a xerogel-hydrogel system that can release the polypeptide in a continuous sustained manner over an extended period of time. See, for example, U.S. Pat. No. 5,226,325, and PCT Publication No. WO 2004/071736.

Liquid polymerizable materials useful in the preparation of hydrogel tubes include a wide variety of polymerizable hydrophilic, and ethylenically unsaturated compounds. See, for example, the compounds listed in PCT Publication No. WO 2008/061355. Mixtures of such hydrophilic monomers typically are used in the polymerization reaction. The type and proportion of monomers are selected to yield a polymer (e.g., a crosslinked homogeneous polymer) that on hydration possesses the desired characteristics (e.g., equilibrium water content (EWC) value and/or pore size) for the contemplated application or use.

In some cases, the polymerization of hydrophilic monomeric mixtures can result in homogeneous hydrophilic copolymers which dissolve, to a varying extent, in an aqueous medium. In such cases, a small amount (e.g., up to about 3 percent) of a copolymerizable polyethylenically unsaturated crosslinking agent can be included in the monomeric mixture to obtain homogeneous crosslinked copolymers that are water-insoluble as well as water-swellable. A slightly crosslinked homopolymer of (hydroxyethyl)methacrylate (HEMA) has an EWC value of about 38%. Crosslinked copolymers of HEMA and N-(2-hydroxypropyl) methacrylamide (HPMA) have EWC values below 38%, while crosslinked copolymers of HEMA and acrylamide exhibit EWC values above 38 w/v %. Therefore, depending on the useful or effective elution rate of the polypeptide, copolymer hydrogels can be customized to elute the polypeptide at the desired rate. Typically, copolymers contain about 15 to about 70 weight % of HEMA units and from about 85 to 30 weight % of a second ethylenic monomer, and thus possess EWC values in the range of from about 20% to about 75%. In some embodiments, a mixture of copolymers can further contain a small amount of a polyethylenically unsaturated crosslinking agent [e.g., ethyleneglycol dimethacrylate ("EDMA") or trimethylolpropane trimethacrylate ("TMPTMA")].

In some embodiments, a pharmaceutical composition for controlled release delivery of a polypeptide in a subject can include (a) a complex of the polypeptide (where the polypeptide has at least one basic functional group) and a polyanion derived from hexahydroxycyclohexane (where the polyanion has at least two negatively charged functional groups); and (b) a pharmaceutically acceptable carrier containing a biodegradable, water-insoluble polymer. Such compositions are described in, for example, PCT Publication No. WO 2006/017852, and can be prepared in the form of solutions, suspensions, dispersions, emulsions, drops, aerosols, creams, semisolids, pastes, capsules, tablets, solid implants, or microparticles, for example. The term "controlled release delivery," as used herein, refers to continual delivery of a pharmaceutical agent in vivo over a period of time (e.g., several days to weeks or months) following administration. Sustained controlled release delivery of an MANP polypeptide can be demonstrated by, for example, continued therapeutic effects of the polypeptide over time (e.g., continued reductions in symptoms over time). Sustained delivery of the polypeptide also can be demonstrated by detecting the presence of the polypeptide in vivo over time. The compositions can provide a low initial burst delivery, followed by stable, controlled release of the polypeptide in vivo for prolonged periods of time (e.g., from days to months).

In such embodiments, a physically and chemically stable complex can form upon appropriate combining of a polypeptide and a polyanion. The complex can take the form of a precipitate that is produced upon combining an aqueous preparation of the polypeptide and the polyanion. Optionally, one or more pharmaceutically acceptable excipients can be incorporated into the complex. Such excipients can function as stabilizers for the polypeptide and/or the complex. Non-limiting examples of suitable excipients include sodium bisulfite, p-aminobenzoic acid, thiourea, glycine, methionine, mannitol, sucrose, and PEG.

A stable complex between a polypeptide and a polyanion can be incorporated into a pharmaceutically acceptable carrier containing a biodegradable water-insoluble polymer, optionally with one or more excipients. The term "biodegradable water-insoluble polymer" refers to biocompatible and/or biodegradable synthetic and natural polymers that can be used in vivo. The term also is meant to include polymers that are insoluble or become insoluble in water or biological fluid at 37° C. The polymers can be purified (e.g., to remove monomers and oligomers) using techniques known in the art. See, e.g., U.S. Pat. No. 4,728,721. Examples of useful polymers include, without limitation, polylactides, polyglycolides, poly(lactide-co-glycolide)s, polycaprolactones, polydioxanones, polycarbonates, polyhydroxybutyrates, polyalkylene oxalates, polyanhydrides, polyamides, polyesteramides, polyurethanes, polyacetals, polyorthocarbonates, polyphosphazenes, polyhydroxyvalerates, polyalkylene succinates, and polyorthoesters, and copolymers, block copolymers, branched copolymers, terpolymers, and combinations thereof.

Biodegradable water-insoluble polymers also can include end capped, end uncapped, or mixtures of end capped and end uncapped polymers. An end capped polymer generally is defined as having capped carboxyl end groups, while an uncapped polymer has free carboxyl end groups.

Factors to consider when determining suitable molecular weights for the polymer can include desired polymer degradation rate, mechanical strength, and rate of dissolution of polymer in solvent. Useful molecular weights for polymers can be from about 2,000 Daltons to about 150,000 Daltons, for example, with a polydispersity of from 1.1 to 2.8, depending upon which polymer is selected for use.

The pharmaceutically acceptable carrier can be a carrier with environment responsive properties (e.g., thermosensitive, pH sensitive, or electrical sensitive), in the form of an injectable solution or suspension, particle, film, pellet, cylinder, disc, microcapsule, microsphere, nanosphere, microparticle, wafer, micelle, liposome, or any other polymeric configuration useful for drug delivery.

Methods of forming various pharmaceutically acceptable polymer carriers include those that are known in the art. See, for example, U.S. Patent Nos. 6,410,044; 5,698,213; 6,312,679; 5,410,016; 5.529,914; 5,501,863; 4,938,763; 5,278,201; and 5,278,202; and PCT Publication No. WO 93/16687.

Compositions can be produced when a polypeptide/polyanion complex is dispersed in a polymeric matrix to form a solid implant, which can be injected or implanted into a subject. Such implants can be prepared using conventional polymer melt-processing techniques, such as extrusion, compression molding, and injection molding, for example.

Preparations of such implants can be carried out under aseptic conditions, or alternatively by terminal sterilization by irradiation (e.g., using gamma irradiation or electron beam sterilization).

In some embodiments, compositions in the form of microspheres can be produced by encapsulating a polypeptide/polyanion complex in a polymeric carrier, using various biocompatible and/or biodegradable polymers having properties that are suitable for delivery to different biological environments or for effecting specific functions. The rate of dissolution and, therefore, delivery of polypeptide is determined by factors such as the encapsulation technique, polymer composition, polymer crosslinking, polymer thickness, polymer solubility, and size and solubility of polypeptide/polyanion complex.

To prepare such microspheres, a polypeptide/polyanion complex to be encapsulated can be suspended in a polymer solution in an organic solvent, such that the polymer solution completely coats the polypeptide/polyanion complex. The suspension then can be subjected to a microencapsulation technique such as spray drying, spray congealing, emulsion, or solvent evaporation emulsion. For example, the suspended complexes or microparticles along with the polymer in an organic solvent can be transferred to a larger volume of an aqueous solution containing an emulsifier, such that the organic solvent evaporates or diffuses away from the polymer and the solidified polymer encapsulates the polypeptide/polyanion complex.

Emulsifiers useful to prepare encapsulated polypeptide/polyanion complexes include poloxamers and polyvinyl alcohol, for example. Organic solvents useful in such methods include acetic acid, acetone, methylene chloride, ethyl acetate, chloroform, and other non-toxic solvents that will depend on the properties of the polymer. Solvents typically are chosen that solubilize the polymer and are ultimately non-toxic.

In some embodiments, a polypeptide can be formulated in a depot, which can provide constantly high exposure levels and may reach high exposure levels rapidly (with a short or no lag phase). See, e.g., U.S. Publication No. 2010/0266704. Depot formulations can include an MANP polypeptide or a pharmaceutically-acceptable salt thereof (e.g., an acid addition salt with an inorganic acid, polymeric acid, or organic acid). Acid addition salts can exist as mono- or divalent salts, depending on whether one or two acid equivalents are added.

As described in U.S. Publication No. 2010/0266704, depot formulations can contain two different linear poly(lactic-co-glycolic acid) (PLGA) polymers having a molar ratio of lactide:glycolide comonomer (L:G) from 85:15 to 65:35, where at least one of the polymers has a low inherent viscosity. Such formulations can provide sustained high plasma levels of the polypeptide for extended periods of time. Examples of suitable polymers include the linear poly(D,L-lactide) and poly(D,L-lactide-co-glycolide) polymers sold under the trade names RESOMER®, LACTEL®, and MIEDISORB® by Boehringer Ingelheim Pharma GmBH & Co. KG (Ingelheim, Germany), Absorbable Polymers International (Pelham, Ala.), and Alkermes, Inc. (Cambridge, Mass.), respectively.

High exposure depot formulations for subcutaneous administration can show immediate or at least very rapid action, such that therapeutic plasma concentrations are achieved in a short time (e.g., one, two, three, four, five, six, or seven days after subcutaneous injection), and can show constantly high exposure levels over about one month or longer.

In some embodiments, the depot formulations provide herein can contain two different PLGA polymers mixed or blended in a % wt ratio of 95:5 to 50:50 (e.g., 85:15 to 50:50, 80:20 to 60:40, 90:10, 85:15, 80:20, 75:25, 70:30, 65:35, 60:40, 55:45 or 50:50% wt). In some embodiments, the polymer with the higher inherent viscosity can have a higher % wt than the polymer with the lower inherent viscosity. In some embodiments, the polymer with the higher inherent viscosity can have an ester end-group. Depot formulations can contain further polymers, including other linear or star shaped PLGA polymers, or poly(D,L-lactide-co-glycolide) (PLG) or polylactic acid (PLA) polymers, provided that favorable PK properties are retained.

The polypeptide content of the depot formulation (the loading) can be in a range of 1% to 30% (e.g., 10% to 25%, more preferred 15% to 20%. The loading is defined as the weight ratio of polypeptide to the total mass of the PLGA formulation.

Depot compositions can be manufactured aseptically, or can be manufactured non-aseptically and terminally sterilized (e.g., using gamma irradiation). Terminal sterilization can result in a product with the highest sterility assurance possible.

Depot compositions also can contain one or more pharmaceutical excipients that can modulate the release behavior of the polypeptide. Such excipients can be present in the composition in an amount of about 0.1% to about 50%. Suitable excipients include, without limitation, polyvinyl alcohol, polyvinyl pyrrolidone, carboxymethyl cellulose sodium, dextrin, PEG, surfactants such as poloxamers (also known as poly(oxyethylene-block-oxypropylene), poly(oxyethylene)-sorbitan-fatty acid esters commercially available under the trade name TWEEN sorbitan fatty acid esters, lecithins, inorganic salts such as zinc carbonate, magnesium hydroxide, magnesium carbonate, protamine, and natural or synthetic polymers bearing amine-residues such as polylysine.

Depot compositions can contain a mixture or blend of different polymers in terms of compositions, molecular weight and/or polymer architectures. A polymer blend is defined herein as a solid solution or suspension of two different linear polymers in one implant or microparticle. A mixture of depots is defined herein as a mixture of two depot-like implants or microparticles or semisolid formulations of different composition with one or more PLGAs in each depot. Pharmaceutical depot compositions in which two PLGAs are present as a polymer blend can be particularly useful.

Pharmaceutical depot compositions can be in the form of implants, semisolids (gels), liquid solutions, microparticles, or suspensions that solidify in situ once they are injected. The following paragraphs are focused on polymer microparticles, although the descriptions also are applicable for implants, semisolids, and liquids.

Microparticles can have a diameter from a few submicrons to a few millimeters (e.g., from about 0.01 micron to about 2 mm, about 0.1 micron to about 500 microns, about 10 to about 200 microns, about 10 to about 130 microns, or about 10 to about 90 microns).

In some embodiments, microparticles can be mixed or coated with an anti-agglomerating agent. Suitable anti-agglomerating agents include, for example, mannitol, glucose, dextrose, sucrose, sodium chloride, and water soluble polymers such as polyvinyl alcohol, polyvinyl pyrrolidone and PEG.

Microparticles can be manufactured using processes known in the art, such as coacervation or phase separation, spray drying, or water-in-oil (W/O), water-in-oil-in-water (W/O/W), or solids-in-oil-in-water (S/O/W) emulsion/suspension methods followed by solvent extraction or solvent evaporation. Emulsion/suspension methods can be particularly useful, and can include the following steps:
  (i) preparing an internal organic phase, comprising
    (a) dissolving a polymer or polymers in a suitable organic solvent (e.g., ethyl acetate, acetone, THF, acetonitrile, or a halogenated hydrocarbon such as methylene chloride, chloroform, or hexafluoroisopropanol) or solvent mixture, and optionally dissolving/dispersing suitable additives;
    (b) dissolving/suspending/emulsifying a polypeptide in the polymer solution obtained in step (a);
  (ii) preparing an external aqueous phase containing one or more stabilizers (e.g., poly(vinylalcohol), hydroxyethyl cellulose, hydroxypropyl cellulose, poly(vinyl pyrolidone), or gelatin) and optionally a buffer salt;
  (iii) mixing the internal organic phase with the external aqueous phase to form an emulsion; and
  (iv) hardening the microparticles by solvent evaporation or solvent extraction, washing the microparticles (e.g., with water), collecting and drying the microparticles (e.g., by freeze-drying or drying under vacuum), and sieving the microparticles (e.g., through 140 µm).

A dry microparticle composition can be terminally sterilized by gamma irradiation, either in bulk or after dispensing into the final container. In some embodiments, bulk sterilized microparticles can be resuspended in a suitable vehicle and dispensed into a suitable device such as double chamber syringe with subsequent freeze drying.

In some embodiments, microparticle depot compositions can include a vehicle to facilitate reconstitution. In addition, prior to administration, microparticles can be suspended in a suitable vehicle for injection (e.g., a water-based vehicle containing one or more pharmaceutical excipients such as mannitol, sodium chloride, glucose, dextrose, sucrose, or glycerin, and/or one or more non-ionic surfactants such as a poloxamer, poly(oxyethylene)-sorbitan-fatty acid ester, carboxymethyl cellulose sodium, sorbitol, poly(vinylpyrrolidone), or aluminium monostearate).

Also provided herein are articles of manufacture containing one or more natriuretic polypeptides or pharmaceutical compositions as described herein (e.g., a depot formulation containing a variant MANP polypeptide) in a vial, syringe, or other vessel. The article of manufacture also can include a transfer set and/or a water-based vehicle in a separate vessel, or the polypeptide/composition and vehicle can be separated in a double chamber syringe.

This disclosure also provides methods for treating cardiovascular disorders (e.g., hypertension, resistant hypertension, and myocardial infarction), cardiorenal disease, and metabolic disorders (e.g., type II diabetes and obesity) in a mammal by administration (e.g., subcutaneous administration) of a natriuretic polypeptide as provided herein. The terms "treat" and "treatment" as used herein refer to prescribing, administering, or providing a medication to beneficially affect or alleviate one or more symptoms associated with a disease or disorder, or one or more underlying causes of a disease or disorder.

Before administering a polypeptide or composition provided herein to a mammal, the mammal can be assessed to determine whether or not the mammal has a need for treatment of a cardiovascular, cardiorenal, or metabolic disorder. After identifying a mammal as having a need for such treatment, the mammal can be treated with a composition provided herein. For example, a composition containing a natriuretic polypeptide can be administered to a mammal in any amount, at any frequency, and for any duration effective to achieve a desired outcome (e.g., to reduce one or more symptoms of a cardiovascular, cardiorenal, or metabolic disease, or to prevent or delay worsening of one or more such symptoms).

In some embodiments, a natriuretic polypeptide or a composition containing a natriuretic polypeptide can be administered at a dose of at least about 0.01 ng natriuretic polypeptide/kg to about 100 mg natriuretic polypeptide/kg of body mass (e.g., about 10 ng natriuretic polypeptide/kg to about 50 mg natriuretic polypeptide/kg, about 20 ng natriuretic polypeptide/kg to about 10 mg natriuretic polypeptide/kg, about 0.1 ng natriuretic polypeptide/kg to about 20 ng natriuretic polypeptide/kg, about 3 ng natriuretic polypeptide/kg to about 10 ng natriuretic polypeptide/kg, or about 50 ng natriuretic polypeptide/kg to about 100 µg/kg) of body mass, although other dosages also may provide beneficial results. A composition can be administered at a dose of, for example, about 0.1 ng natriuretic polypeptide/kg/minute to about 500 ng natriuretic polypeptide/kg/minute (e.g., about 0.5 ng natriuretic polypeptide/kg/minute, about 1 ng natriuretic polypeptide/kg/minute, about 2 ng natriuretic polypeptide/kg/minute, about 3 ng natriuretic polypeptide/kg/minute, about 5 ng natriuretic polypeptide/kg/minute, about 7.5 ng natriuretic polypeptide/kg/minute, about 10 ng natriuretic polypeptide/kg/minute, about 12.5 ng natriuretic polypeptide/kg/minute, about 15 ng natriuretic polypeptide/kg/minute, about 20 ng natriuretic polypeptide/kg/minute, about 25 ng natriuretic polypeptide/kg/minute, about 30 ng natriuretic polypeptide/kg/minute, about 50 ng natriuretic polypeptide/kg/minute, about 100 ng natriuretic polypeptide/kg/minute, or about 300 ng natriuretic polypeptide/kg/minute).

A polypeptide can be administered once (e.g., by implantation or injection of a depot composition), or more than once (e.g., by repeated injections, or by use of a series of transdermal drug patches). When administered more than once, the frequency of administration can range from about four times a day to about once every other month (e.g., twice a day, once a day, three to five times a week, about once a week, about twice a month, about once a month, or about once every other month). In addition, the frequency of administration can remain constant or can be variable during the duration of treatment. Various factors can influence the actual frequency of administration used for a particular application. For example, the effective amount, duration of treatment, route of administration, and severity of condition may require an increase or decrease in administration frequency.

In some embodiments, a natriuretic polypeptide or a composition containing a natriuretic polypeptide can be administered via a first route (e.g., intravenously) for a first period of time, and then can be administered via another route (e.g., topically or subcutaneously) for a second period of time. For example, a composition containing a natriuretic polypeptide can be intravenously administered to a mammal (e.g., a human) at a dose of about 0.1 ng natriuretic polypeptide/kg/minute to about 300 ng natriuretic polypeptide/kg/minute (e.g., about 1 ng natriuretic polypeptide/kg/minute to about 15 ng natriuretic polypeptide/kg/minute, about 3 ng natriuretic polypeptide/kg/minute to about 10 ng natriuretic polypeptide/kg/minute, or about 10 ng natriuretic polypeptide/kg/minute to about 30 ng natriuretic polypeptide/kg/minute) for one to seven days (e.g., one, two, three, four, five, six, or seven days), and subsequently can be subcutaneously administered to the mammal at a dose of about 10 ng natriuretic polypeptide/kg/day to about 100 ng natriuretic polypeptide/kg/day (e.g., about 10 ng natriuretic polypeptide/kg/day, about 20 ng natriuretic polypeptide/kg/day, about 25 ng natriuretic polypeptide/kg/day, about 30 ng natriuretic polypeptide/kg/day, about 50 ng natriuretic polypeptide/kg/day, or about 100 ng natriuretic polypeptide/kg/day) for five to 30 days (e.g., seven, 10, 14, 18, 21, 24, or 27 days).

The methods provided herein can include administering to a mammal an effective amount of a natriuretic polypeptide (e.g., a variant of MANP) or a nucleic acid encoding such a natriuretic polypeptide, or an effective amount of a composition containing such a natriuretic polypeptide. As used herein, the term "effective amount" is an amount of a molecule or composition that is sufficient to alter a selected parameter by at least 10%. For example, in some embodiments, an "effective amount" of a natriuretic polypeptide can be an amount of the natriuretic polypeptide that is sufficient to increase natriuresis and/or diuresis (or to increase or decrease a characteristic of natriuresis and/or diuresis such as plasma cGMP levels, urinary cGMP excretion, net renal cGMP generation, urine flow, urinary sodium excretion, urinary potassium excretion, hematocrit, plasma BNP immunoreactivity, renal blood flow, plasma ANP immunoreactivity, renal vascular resistance, proximal and distal fractional reabsorption of sodium, mean arterial pressure, pulmonary wedge capillary pressure, right atrial pressure, pulmonary arterial pressure, plasma renin activity, plasma angiotensin II levels, plasma aldosterone levels, renal perfusion pressure, and systemic vascular resistance) by at least 10% (e.g., at least 10%, at least 15%, at least 20%, at least 25%, at least 30%, at least 40%, at least 50%, at least 60%, at least 70%, at least 75%, at least 80%, at least 85%, at least 90%, at least 95%, at least 99%, or 100%), as compared to the level of the same parameter prior to treatment, or as compared to the level of the parameter in a control, untreated mammal. For example, an "effective amount" of a natriuretic polypeptide can be an amount that increases sodium excretion in a treated mammal by at least 10% as compared to the level of sodium excretion in the mammal prior to administration of the natriuretic polypeptide, or as compared to the level of sodium excretion in a control, untreated mammal.

In some embodiments, an "effective amount" of a natriuretic polypeptide can be an amount of the natriuretic polypeptide that is sufficient to reduce the occurrence of a symptom of cardiovascular, metabolic, or cardiorenal disease by at least 10% (e.g., at least 10%, at least 15%, at least 20%, at least 25%, at least 30%, at least 40%, at least 50%, at least 60%, at least 70%, at least 75%, at least 80%, at least 85%, at least 90%, at least 95%, at least 99%, or 100%). In some cases, for example, an "effective amount" of a natriuretic polypeptide as provided herein can be an amount that reduces a symptom of cardiovascular, metabolic, or cardiorenal disease in a treated mammal by at least 10% as compared to the level of the symptom in the mammal prior to administration of the natriuretic polypeptide or without administration of the natriuretic polypeptide, or as compared to the level of the symptom in a control, untreated mammal. The presence or extent of such symptoms can be evaluated using methods such as those known in the art. In some cases, an "effective amount" of a natriuretic polypeptide as provided herein can be an amount that reduces blood pressure in a mammal identified as having hypertension by at least 10% (e.g., at least 15%, at least 20%, at least 25%, at least 30%, at least 40%, or at least 50%) as compared to the blood pressure in the mammal prior to administration of the natriuretic polypeptide or without administration of the natriuretic polypeptide, or as compared to the level of the symptom in a control, untreated mammal.

In some embodiments, the amount and frequency of natriuretic polypeptide administered to a mammal can be titrated in order to, for example, identify a dosage that is most effective to treat hypertension and/or cardiovascular, metabolic, or cardiorenal disease while having the least amount of adverse effects. For example, an effective amount of a composition can be any amount that reduces fibrillation within a mammal without having significant toxicity in the mammal. If a particular mammal fails to respond to a particular amount, then the amount can be increased by, for example, two-fold, three-fold, five-fold, or ten-fold. After receiving this higher concentration, the mammal can be monitored for both responsiveness to the treatment and toxicity symptoms, and adjustments in the dosage can be made accordingly. The effective amount can remain constant or can be adjusted as a sliding scale or variable dose depending on the mammal's response to treatment.

The frequency of administration can be any frequency that reduces a symptom of cardiovascular, metabolic, or cardiorenal disease within a mammal without producing significant toxicity in the mammal. For example, the frequency of administration can be from about four times a day to about once every other month, or from about once a day to about once a month, or from about once every other day to about once a week. In addition, the frequency of administration can remain constant or can be variable during the duration of treatment. As with the effective amount, various factors can influence the actual frequency of administration used for a particular application. For example, the effective amount, duration of treatment, route of administration, and severity of renal condition may require an increase or decrease in administration frequency.

An effective duration of administration can be any duration that reduces hypertension or a symptom of cardiorenal disease within a mammal without producing significant toxicity in the mammal. The effective duration can vary from one to several days, to several weeks, months, or years. In general, the effective duration can range in duration from several days to several months. For example, an effective duration can range from about one to two weeks to about 36 months. Prophylactic treatments can be typically longer in duration and may last throughout an individual mammal's lifetime. Multiple factors can influence the actual effective duration used for a particular treatment or prevention regimen. For example, an effective duration can vary with the frequency of administration, amount administered, route of administration, and severity of a renal condition.

After administering a polypeptide or composition as provided herein to a mammal, the mammal can be monitored to determine whether or not the cardiovascular, cardiorenal, or metabolic disorder has improved. For example, a mammal can be assessed after treatment to determine whether or not one or more symptoms of the disorder have decreased. Any suitable method can be used to assess improvements in function. If a mammal fails to respond to a particular dose, then the amount can be increased by, for example, two-fold, three-fold, five-fold, or ten-fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment.

The methods provided herein can further include monitoring the concentration of the polypeptide in serum or plasma drawn from the patient. Blood can be drawn at regular intervals (e.g., every 15 minutes, 30 minutes, 1 hour, 2 hours, 4 hours, 6 hours, 10 hours, 12 hours, 20 hours, 22 hours, daily, biweekly, weekly, or monthly). Alternatively, blood can be drawn at random intervals. In still another aspect, an additional step may include creating a feedback loop by increasing or decreasing the amount of polypeptide administered after measuring its concentration.

Any suitable method can be used to measure serum levels of a polypeptide provided herein including, without limitation, mass spectrometry and immunological methods such as ELISA. An antibody used in an immunological assay can be, without limitation, a polyclonal, monoclonal, human, humanized, chimeric, or single-chain antibody, or an antibody fragment having binding activity, such as a Fab fragment, F(ab') fragment, Fd fragment, fragment produced by a Fab expression library, fragment comprising a VL or VH domain, or epitope binding fragment of any of the above. An antibody can be of any type, (e.g., IgG, IgM, IgD, IgA or IgY), class (e.g., IgG1, IgG4, or IgA2), or subclass. In addition, an antibody can be from any animal including birds and mammals. For example, an antibody can be a human, rabbit, sheep, or goat antibody. Such an antibody can be capable of binding specifically to a polypeptide provided herein.

Antibodies can be generated and purified using any suitable method, including those known in the art. For example, monoclonal antibodies can be prepared using hybridoma, recombinant, or phage display technology, or a combination of such techniques. In some cases, antibody fragments can be produced synthetically or recombinantly from a gene encoding the partial antibody sequence. In some cases, an antibody fragment can be enzymatically or chemically produced by fragmentation of an intact antibody. An antibody directed against a polypeptide provided herein typically can bind the polypeptide at an affinity of at least $10^4$ mol$^{-1}$ (e.g., at least $10^5$, $10^6$, $10^7$, $10^8$, $10^9$, $10^{10}$, $10^{11}$, or $10^{12}$ mol$^{-1}$).

The invention will be further described in the following example, which does not limit the scope of the invention described in the claims.

EXAMPLE

Figure 2B:
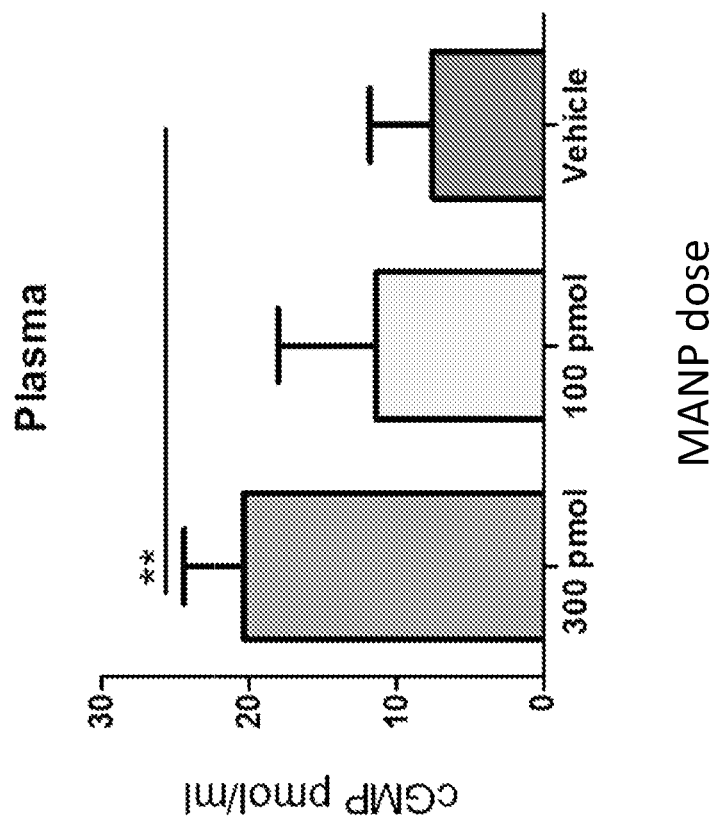
Figure 2D:
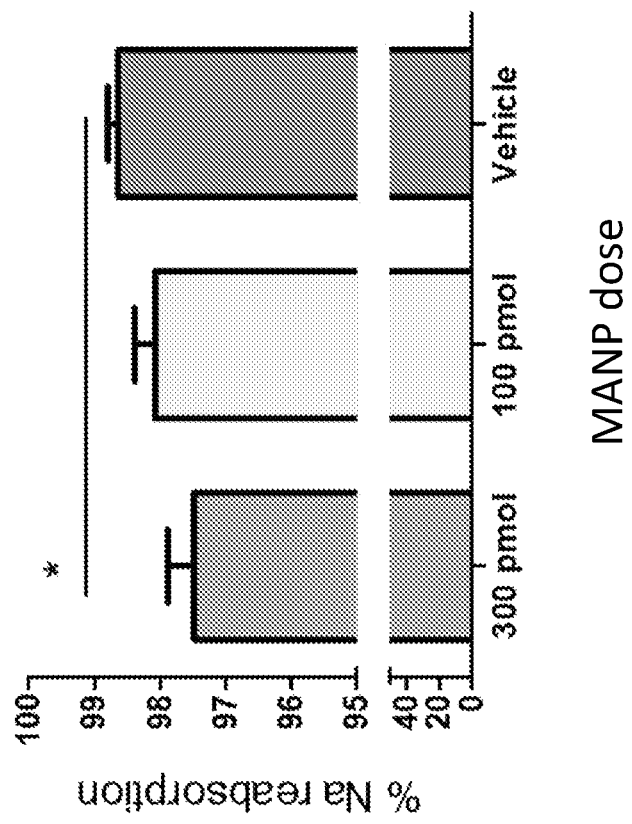
Figure 2E:
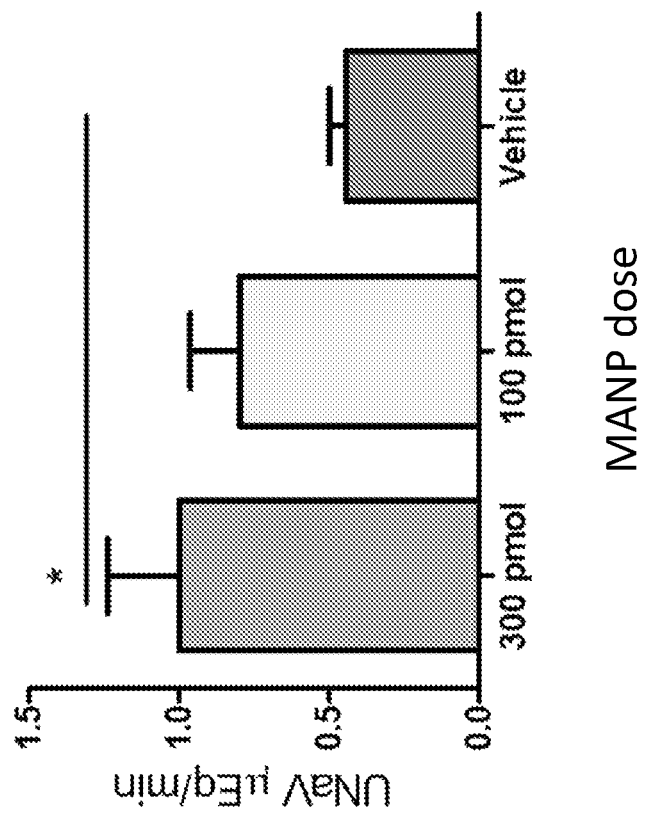

Spontaneously hypertensive rats (SHRs) were injected with intravenous (IV) MANP or vehicle, and BP, plasma and urinary cGMP, and natriuretic effects were determined. These studies revealed that in SHRs, acute IV administration of MANP reduced BP (FIG. 2A), increased plasma and urinary cGMP generation (FIGS. 2B and 2C), and induced natriuresis (FIGS. 2D and 2E), demonstrating the efficacy of using MANP to treat HTN.

Figure 3:
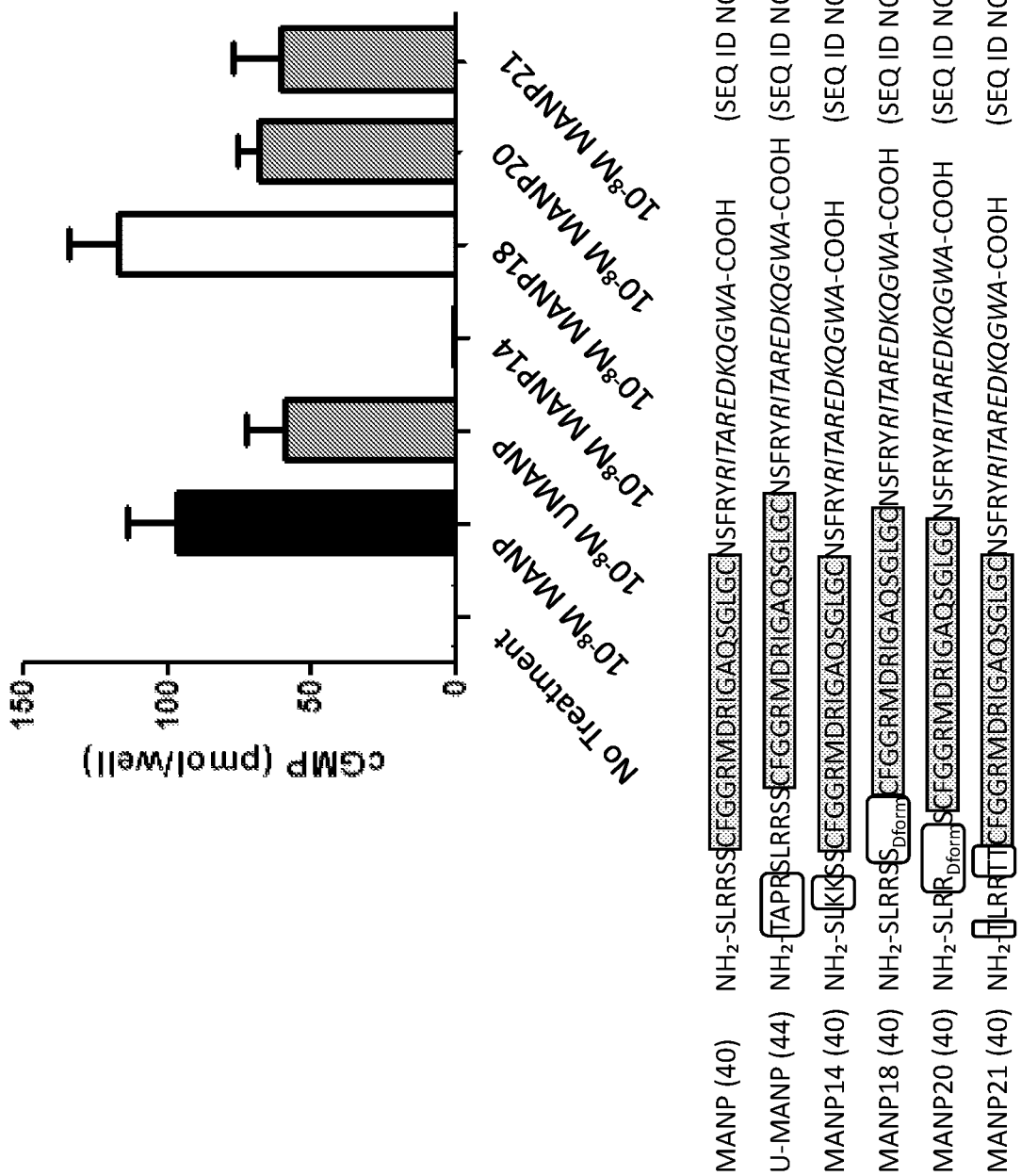
FIG. 3 is a graph plotting cGMP generation in vitro in HEK293 cells overexpressing pGC-A, after treatment with MANP or the indicated MANP variants. The sequences of the variant peptides tested are shown at the bottom of the figure. These include the starting MANP peptide (SEQ ID NO:1), MANP with four additional amino acids from urodilatin at the N-terminus (UMANP; SEQ ID NO:2), MANP with lysine residues substituted for the two arginine residues in the N-terminal portion (MANP14; SEQ ID NO:3), MANP with D-serine at the sixth position (MANP18; SEQ ID NO:4), MANP with D-arginine at the fourth position and the serine at position 5 removed (MANP20; SEQ ID NO:5), and MANP with threonine residues substituted for the three serine residues in the N-terminal portion (MANP21; SEQ ID NO:6)
Figure 5A:
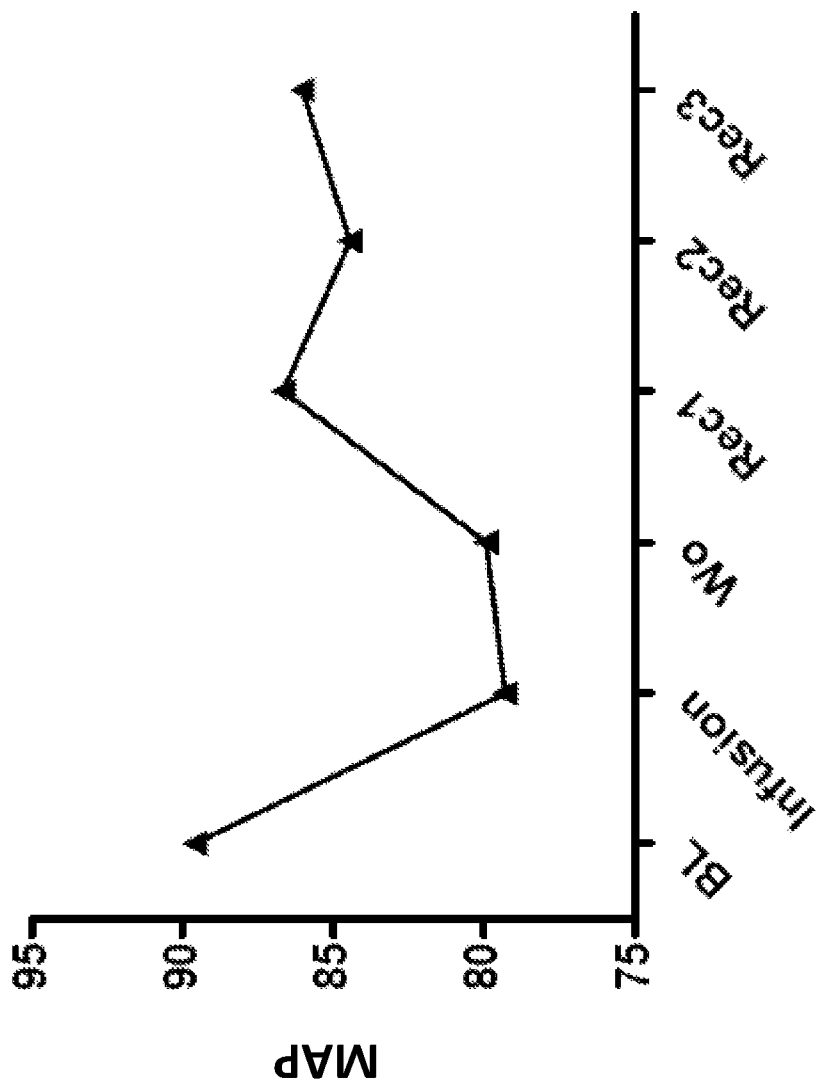
FIGS. 5A-5G are graphs plotting the effect of MANP18 on mean arterial pressure (MAP.
Figure 5B:
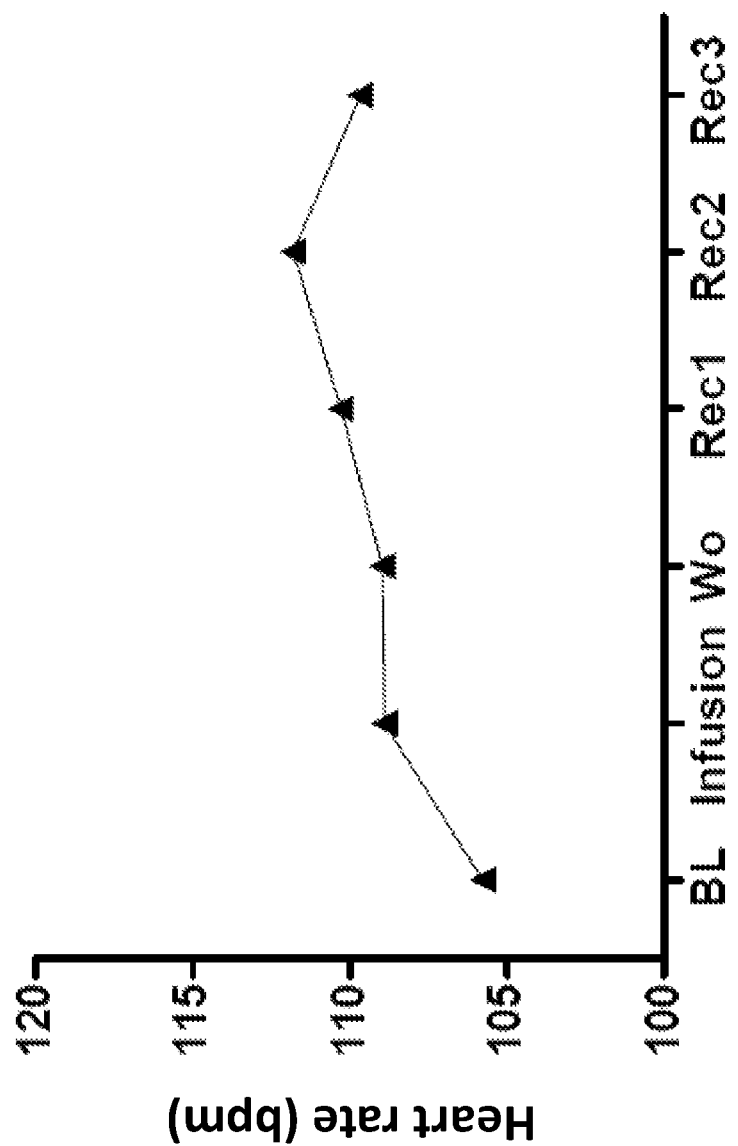
Figure 5C:
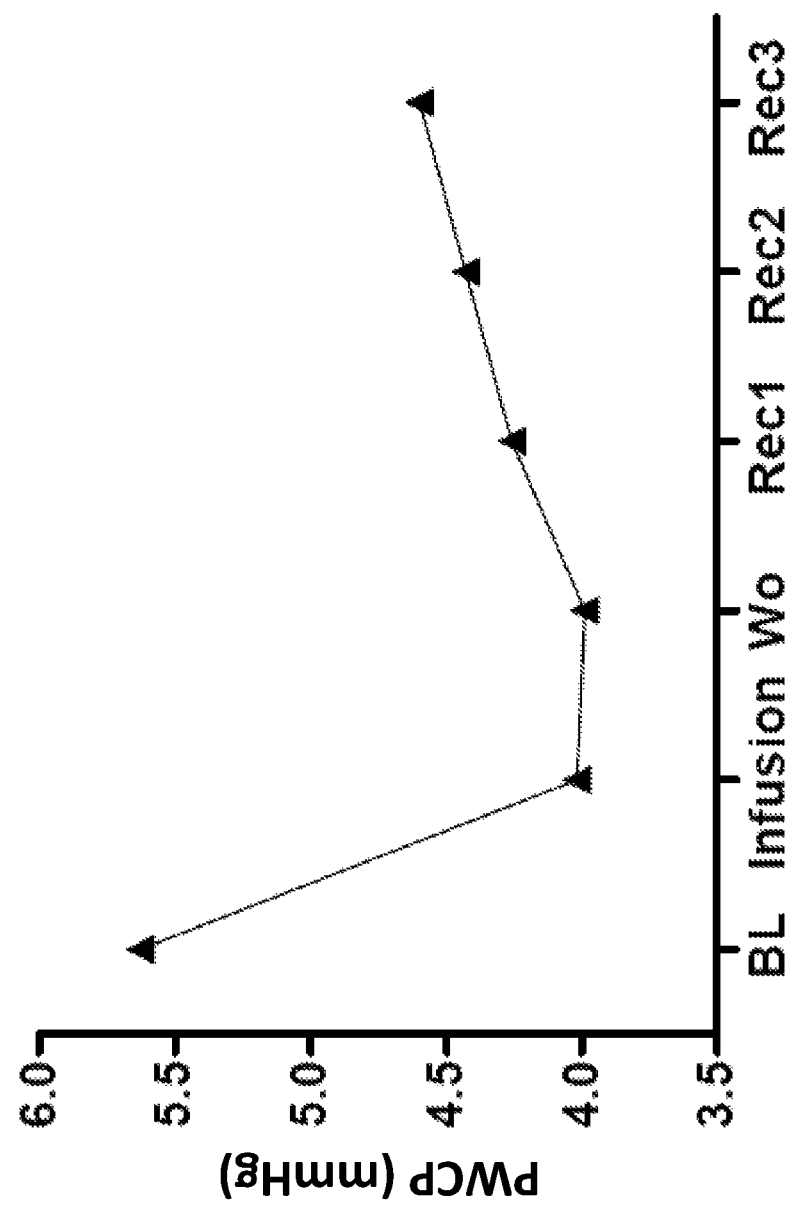
Figure 5D:
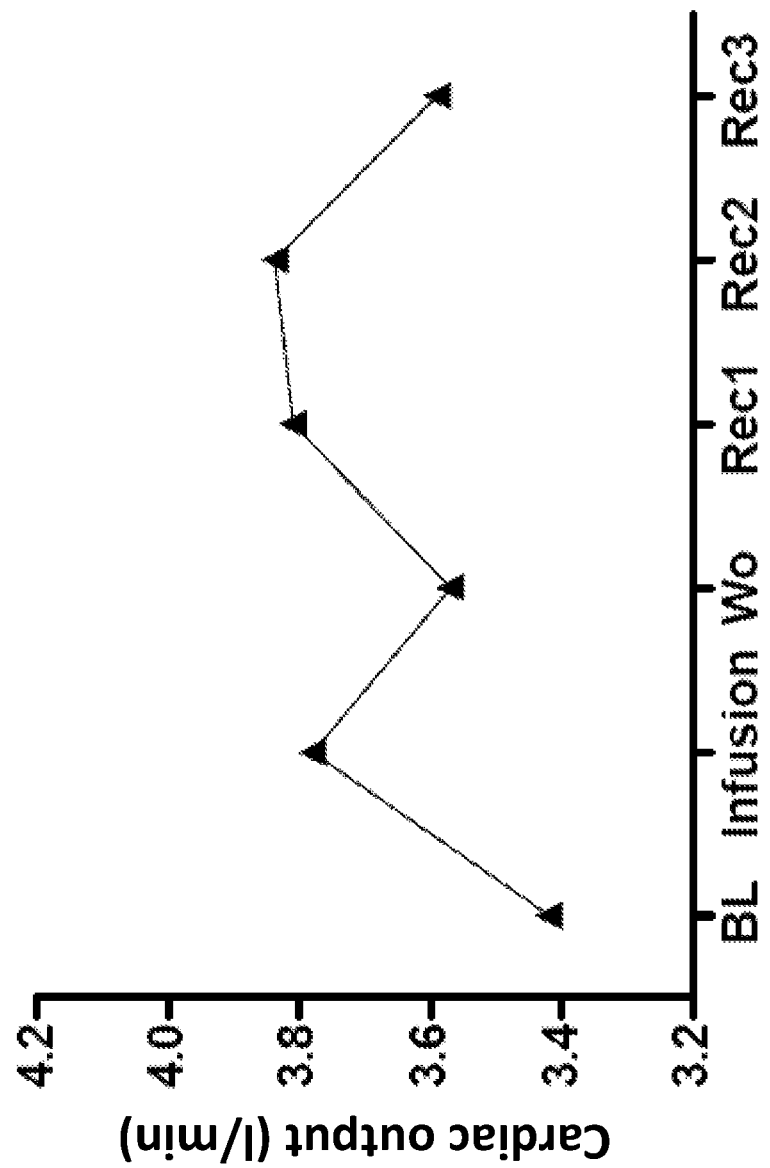
Figure 5E:
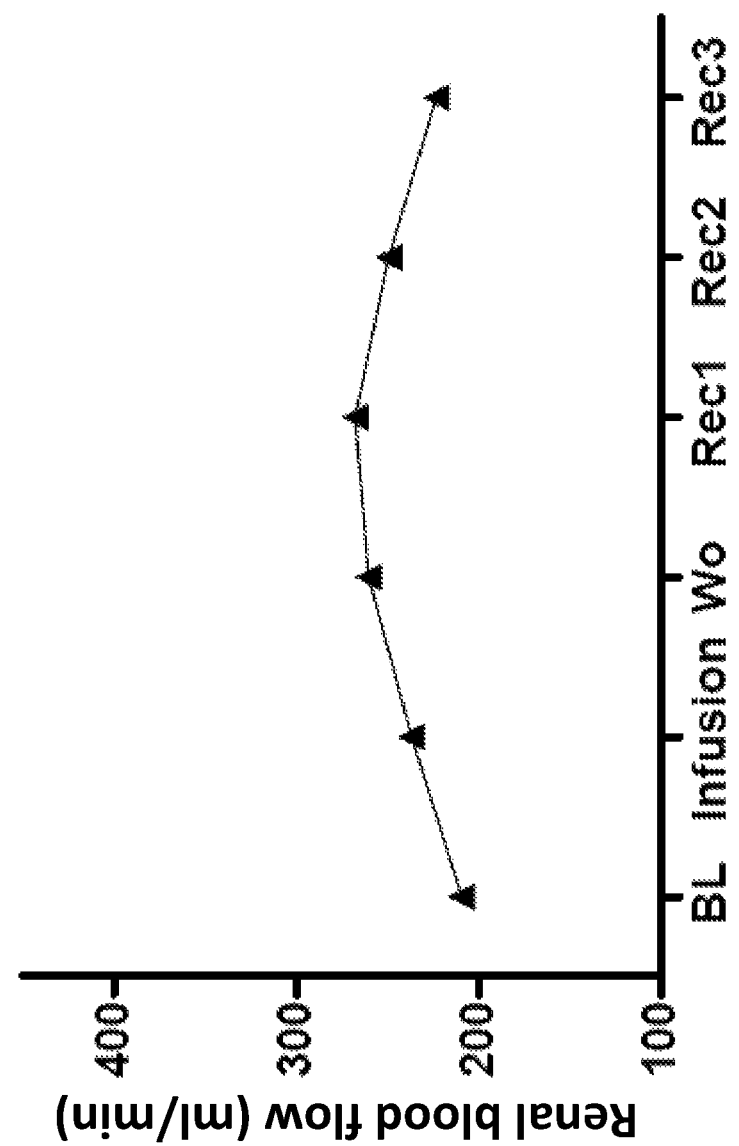
Figure 5F:
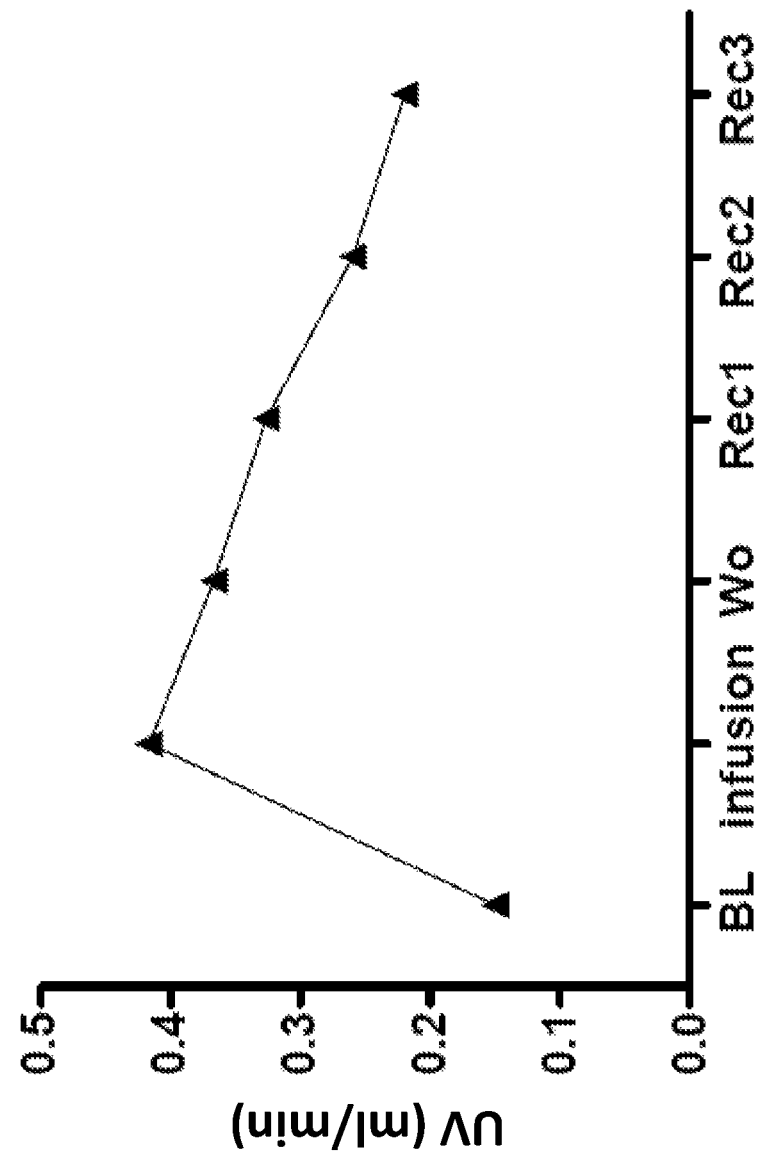
Figure 5G:
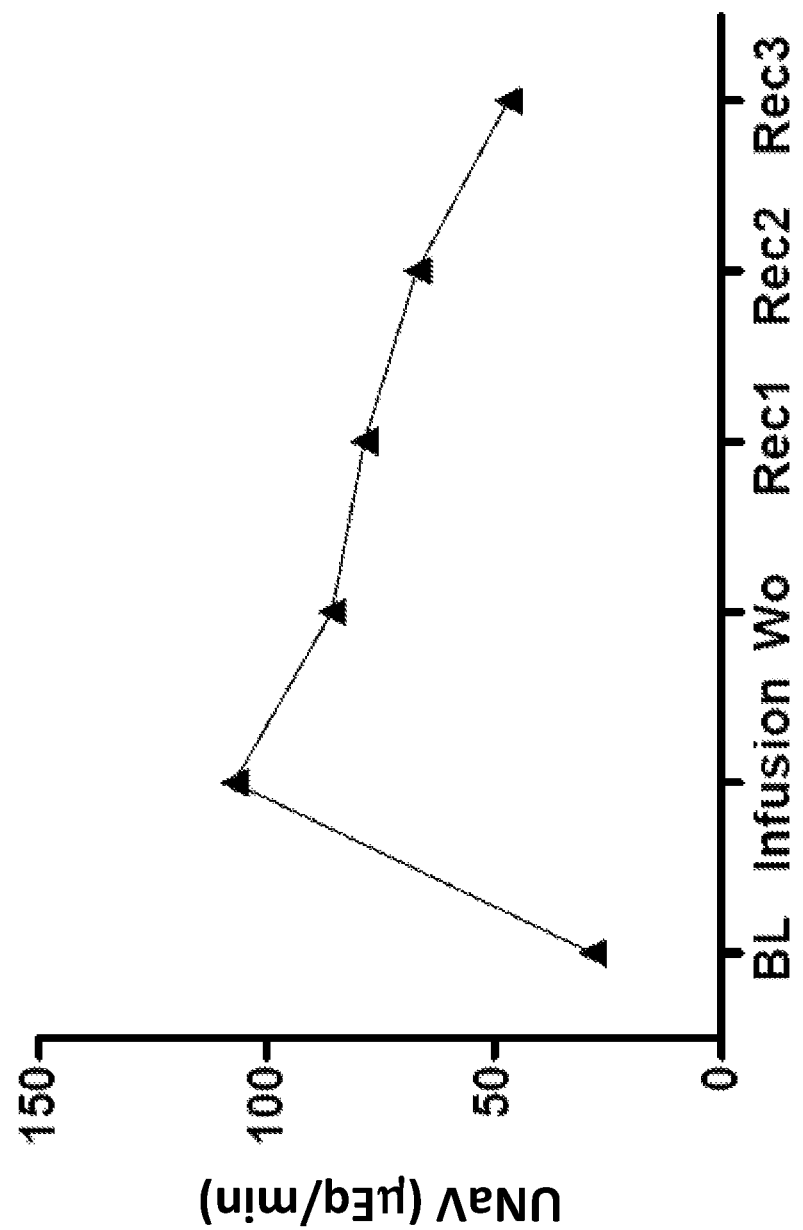

For in vitro studies, five MANP variants were generated that contained substitutions within the N-terminal region. HEK293 cells overexpressing pGC-A were stimulated with MANP or the five variants ($10^{-8}$ M), and intracellular cGMP generation was measured. Key mutations of the NT resulted in loss-of-function (TABLE 2 and FIG. 3), identifying the importance of peptide-receptor dependency. FIG. 4 shows cGMP generation for each analogue as a percentage of cGMP generation for MANP.

These studies demonstrated for the first time in a genetic model of HTN that MANP reduces BP, activates systemic and renal pGC-A/cGMP, and induces natriuresis. Further, enhanced or reduced pGC-A activation with targeted AA mutations in the N-terminal sequence of MANP provided key structure-function insights into MANP, which provide useful to next generation MANP therapeutic peptides.

TABLE 2

| Peptide (SEQ ID NO) | #aa | Potency vs. MANP | Modification vs. MANP |
|---|---|---|---|
| U-MANP (2) | 44 | – | Urodilatin N-terminus added |
| MANP14 (3) | 40 | – | Lys replaces both N-terminal Arg |
| MANP18 (4) | 40 | = | D-form of Ser6 |
| MANP20 (5) | 40 | – | D-form of Arg4 |
| MANP21 (6) | 40 | – | Thr replaces all N-terminal Ser |

SEQ ID NO: 1:
SLRRSSCFGGRMDRIGAQSGLGCNSFRYRITAREDKQGWA

SEQ ID NO: 2:
TAPRSLRRSSCFGGRMDRIGAQSGLGCNSFRYRITAREDKQGWA

SEQ ID NO: 3:
SLKKSSCFGGRMDRIGAQSGLGCNSFRYRITAREDKQGWA

SEQ ID NO: 4:
SLRRSS$_{Dform}$CFGGRMDRIGAQSGLGCNSFRYRITAREDKQGWA

SEQ ID NO: 5:
SLRR$_{Dform}$SCFGGRMDRIGAQSGLGCNSFRYRITAREDKQGWA

SEQ ID NO: 6:
TLRRTTCFGGRMDRIGAQSGLGCNSFRYRITAREDKQGWA

Figure 6A:
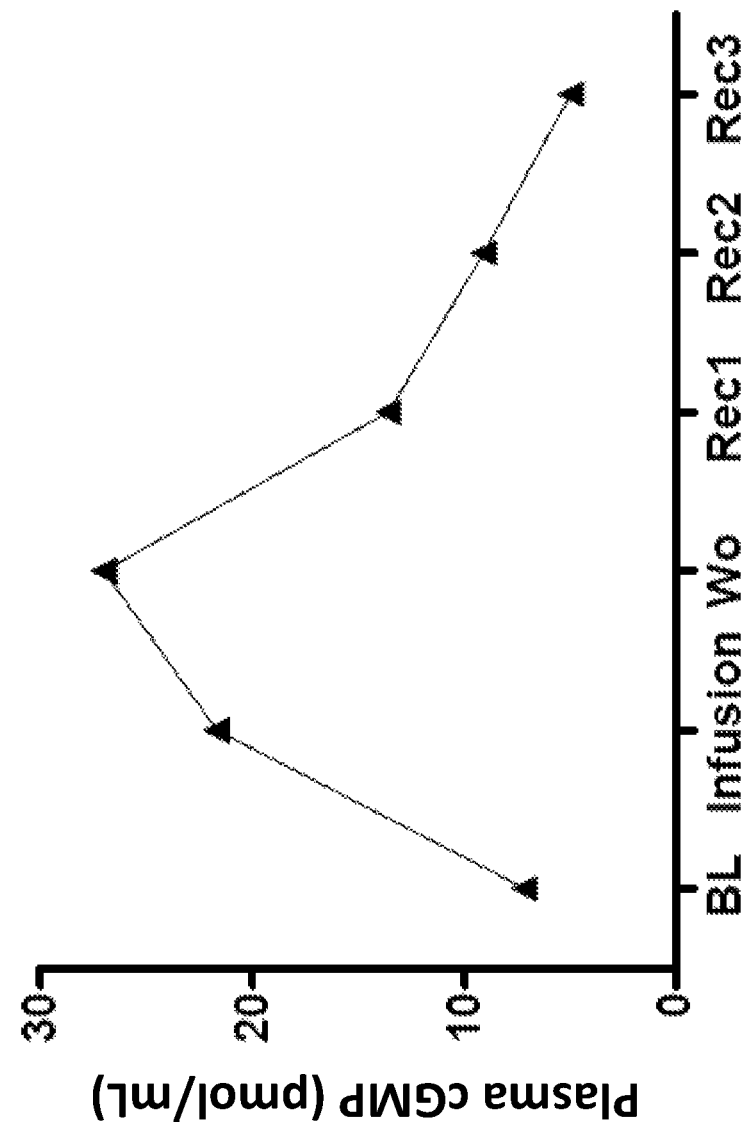
FIGS. 6A-6G are graphs plotting the effect of MANP18 on plasma cGMP levels (FIG. 6A), urinary cGMP excretion (FIG. 6B), plasma ANP levels (FIG. 6C), urinary ANP excretion (FIG. 6D), plasma aldosterone levels (FIG. 6E), plasma renin activity (PRA.
Figure 6B:
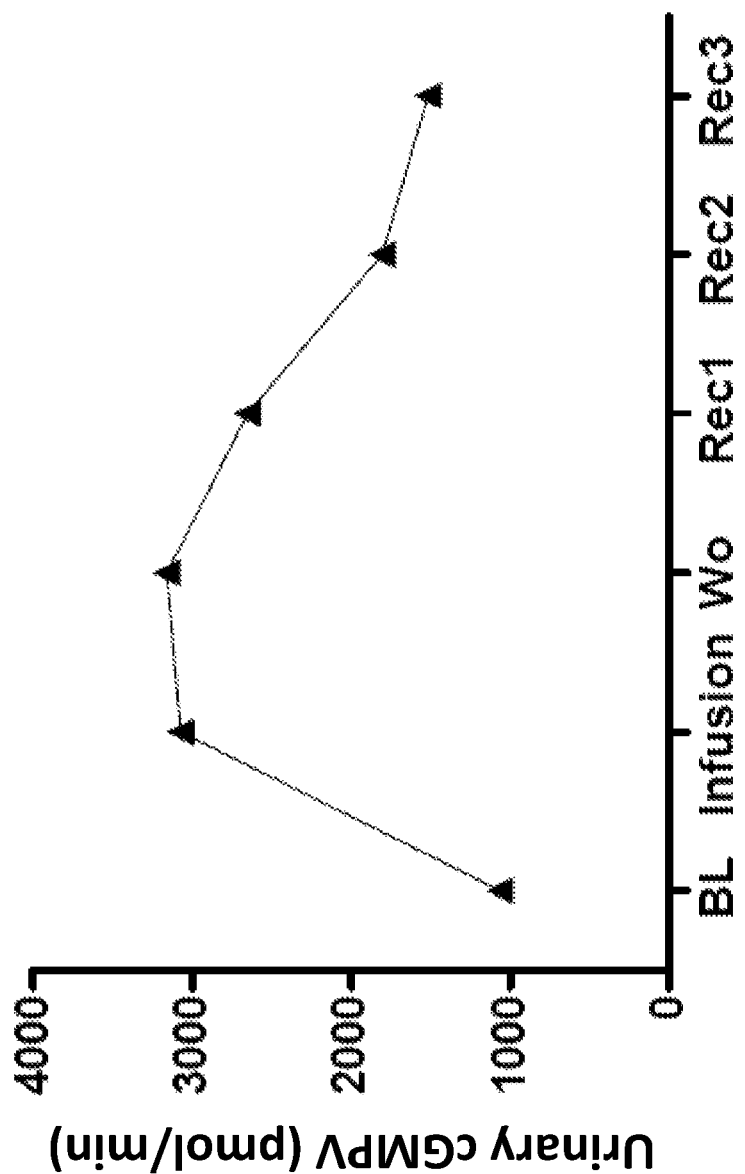
Figure 6C:
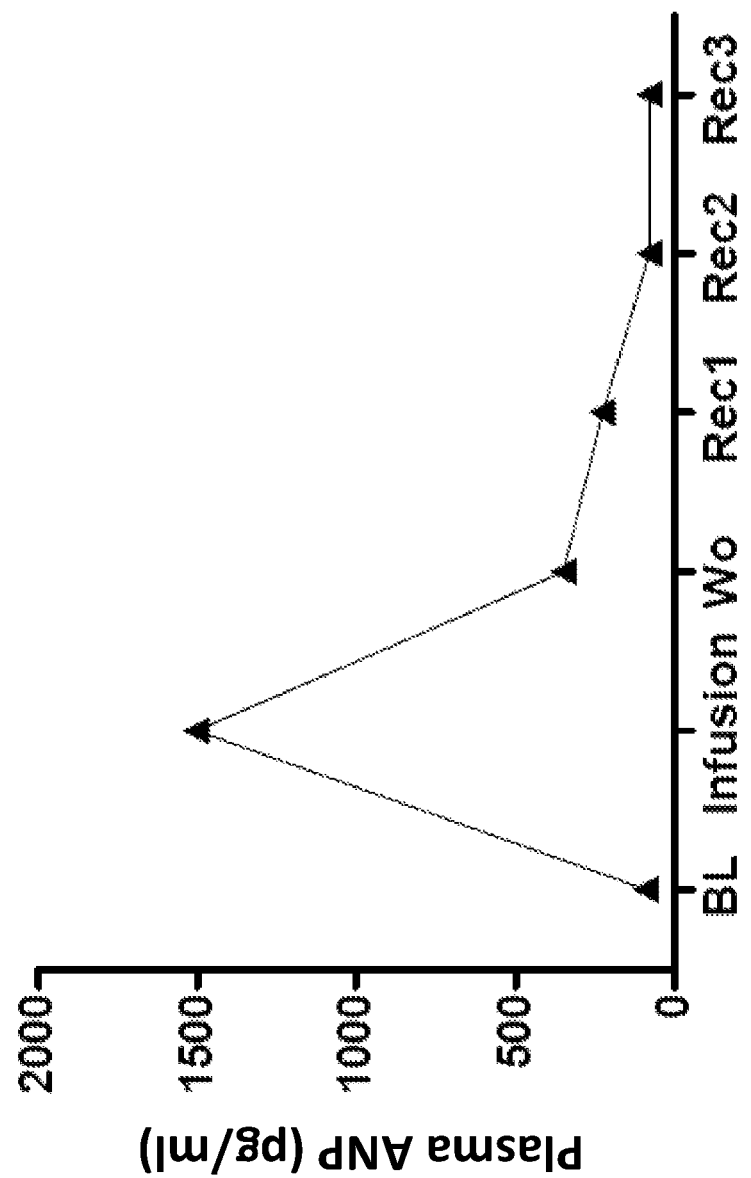
Figure 6D:
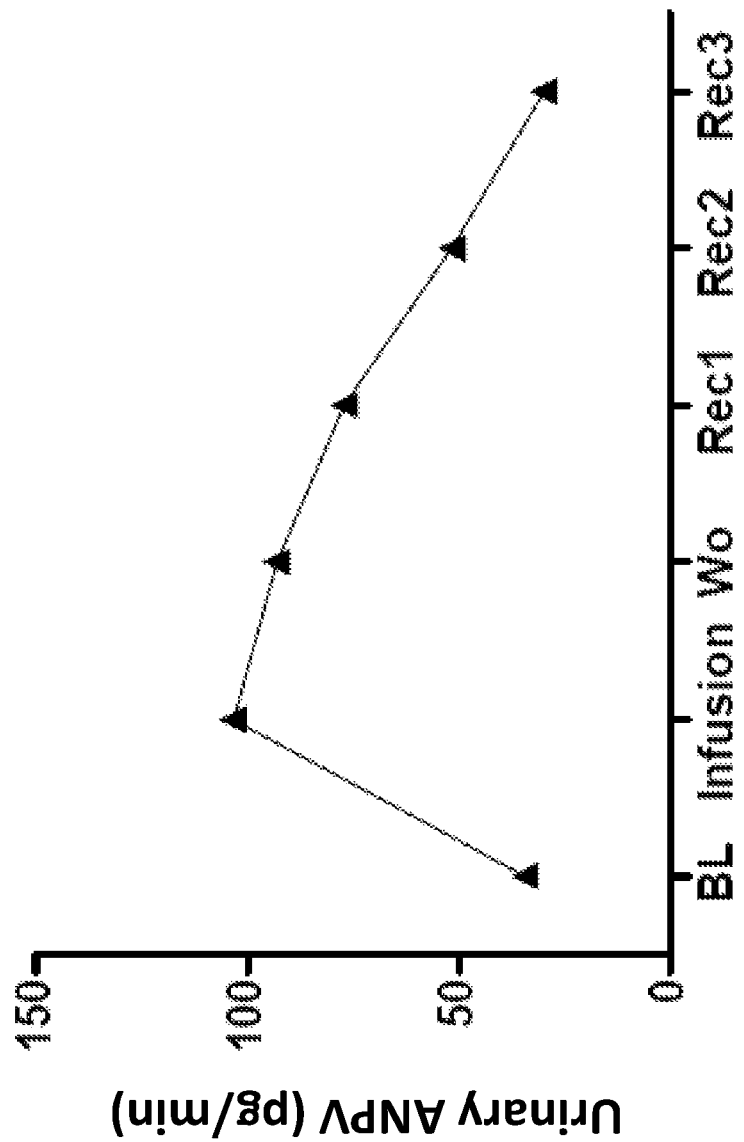
Figure 6E:
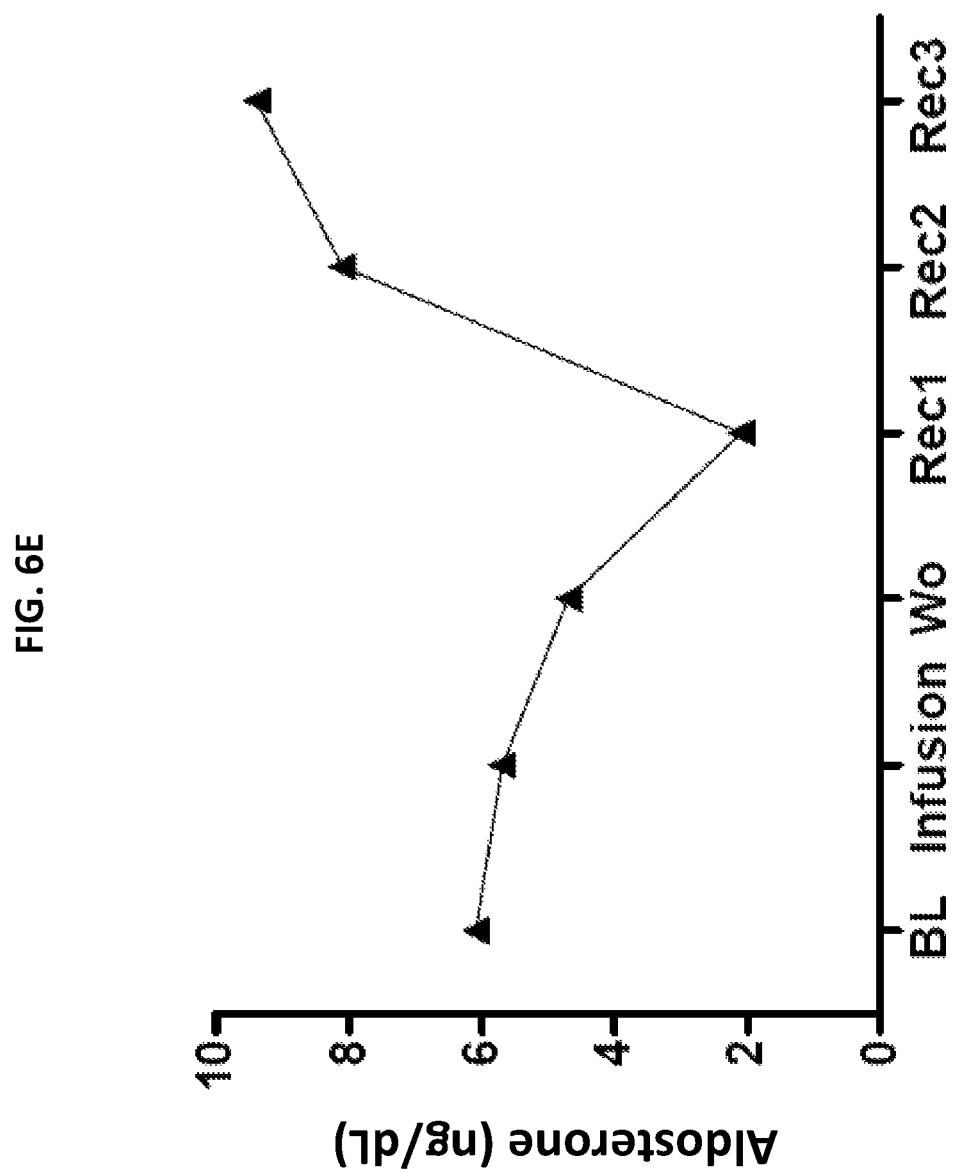
Figure 6F:
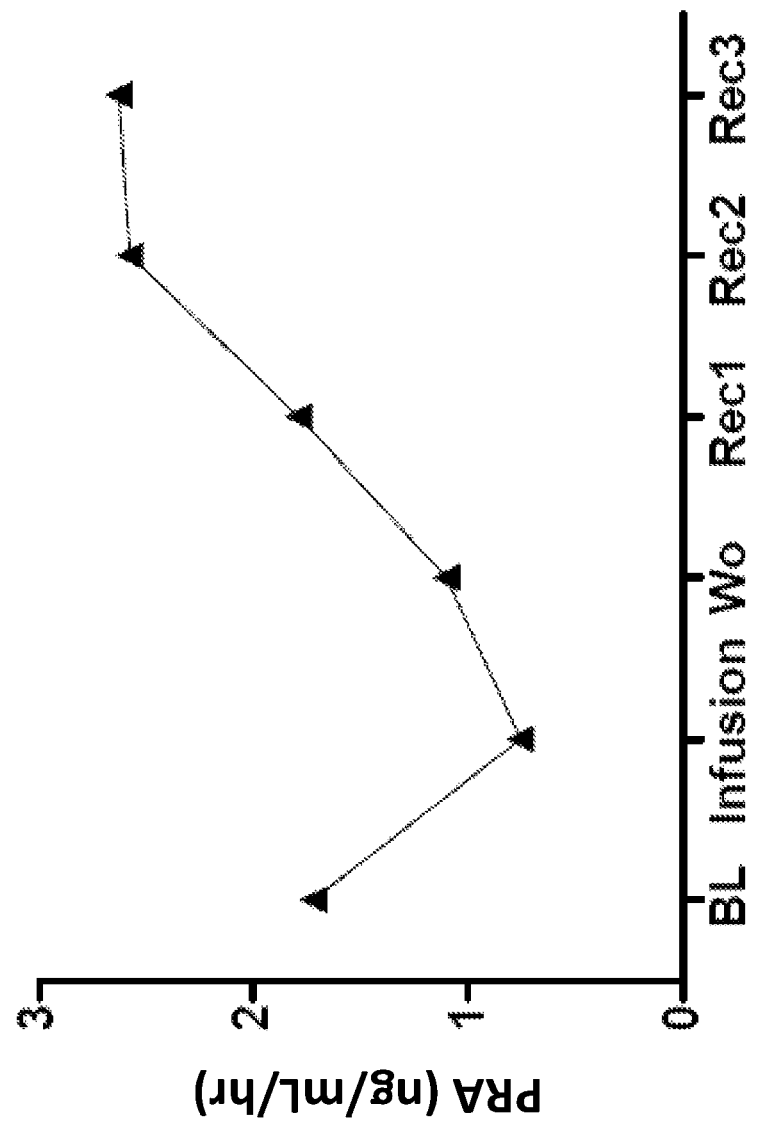
Figure 6G:
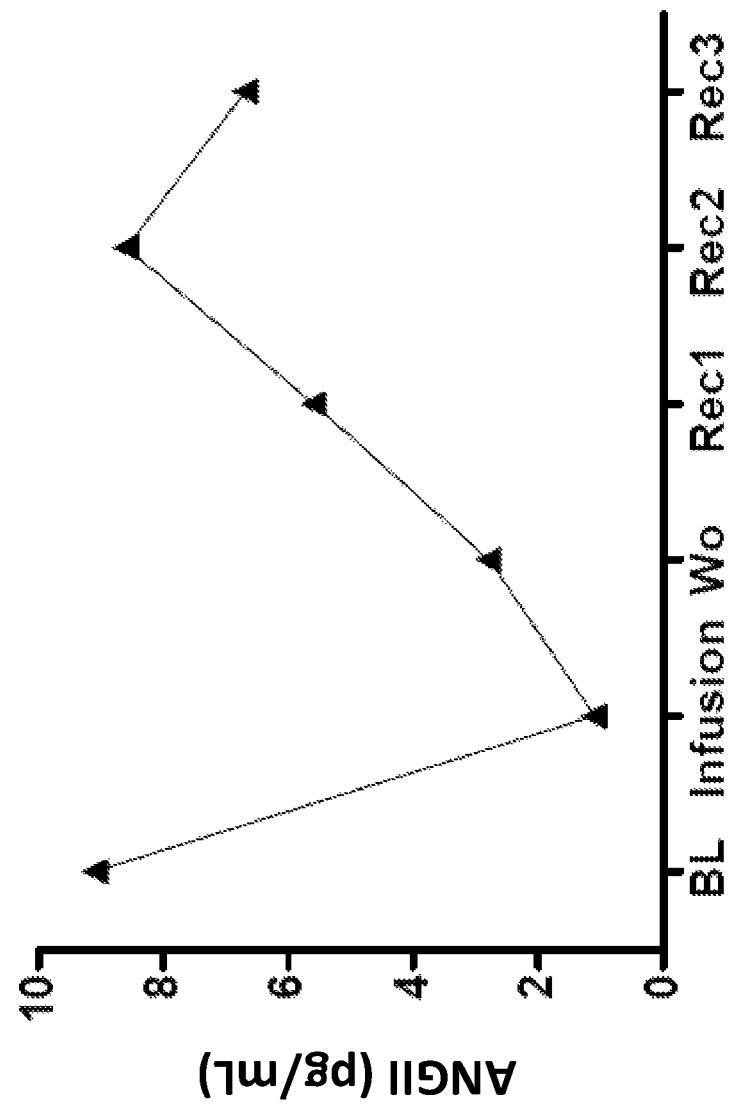

In vivo infusion studies were conducted using MANP18 in a normal canine. The night before the study, the dog was fasted. On the day of the experiment, the dog was anesthetized with pentobarbital sodium (15 mg/kg IV), intubated, and mechanically ventilated with supplemental oxygen (Harvard Respirator; Amersham, MA) at 12 cycles/minute. The femoral artery was cannulated for MAP monitoring and blood sampling, and the femoral vein was cannulated for saline infusion. Through a left lateral flank incision, the left kidney was exposed and the ureter was cannulated for urine sampling. Supplemental nonhypotensive doses of pentobarbital were administered as needed during the study. After 60 minutes of equilibrium, a baseline clearance was performed. All clearances consisted of urine collection over 30 minutes. Arterial blood sampling and hemodynamic measurements were measured midway through each clearance. After the baseline clearance, MANP18 was infused with saline at a dose of 33 pmol peptide/kg/min. The peptide was infused for a total of 45 minutes, which included a 15-minute lead-in period followed by a 30-minute clearance. The peptide infusion was then discontinued, and four 30-minute clearances were performed (washout, recovery 1, recovery 2, and recovery 3). As shown in FIGS. 5A-5G, MANP18 had blood pressure lowering, cardiac output enhancing, and natriuretic actions. In addition, MANP18 activated cGMP (FIGS. 6A and 6B), temporarily increased ANP levels (FIGS. 6C and 6D), and temporarily depressed levels of aldosterone (FIG. 6E), PRA (FIG. 6F), and ANGII (FIG. 6G).

Additional in vitro experiments were conducted using an MANP variant having a tryptophan substitution for the leucine at position 2 of MANP (SWLRRSSCFGGRMDRI GAQSGLGCNSFRYRITA REDKQGWA; SEQ ID NO:15). Human pGC-A and pGC-B cDNA clones were purchased from Origene (Rockville, Md.). HEK293 cells were stably transfected with pGC-A or pGC-B cDNA using LIPOFECTAMINE® (Invitrogen; Grand Island, N.Y.). Transfected cells were maintained in Dulbecco's modified Eagle's medium supplemented with 10% fetal bovine serum, 100

Figure 7A:
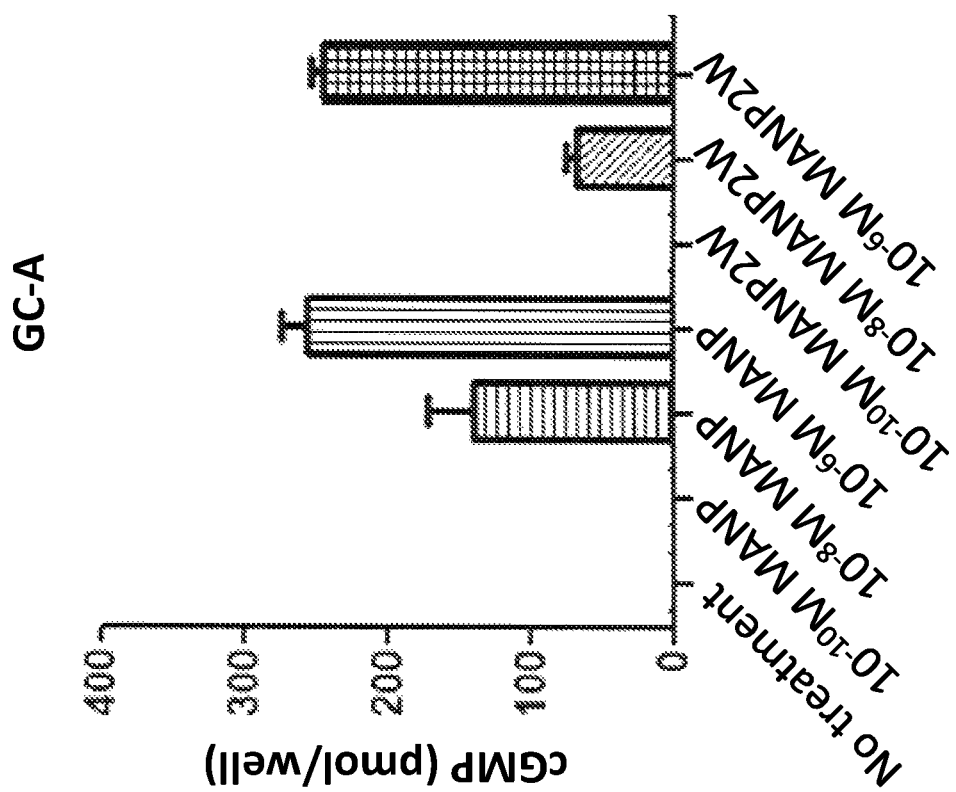
FIGS. 7A and 7B are graphs plotting cGMP generation in vitro in HEK293 cells overexpressing pGC-A (FIG. 7A) or pGC-B (FIG. 7B) after treatment with the indicated amounts of MANP or MANP2W (FIG. 7A), or the indicated amounts of CNP or MANP2W (FIG. 7B).
Figure 7B:
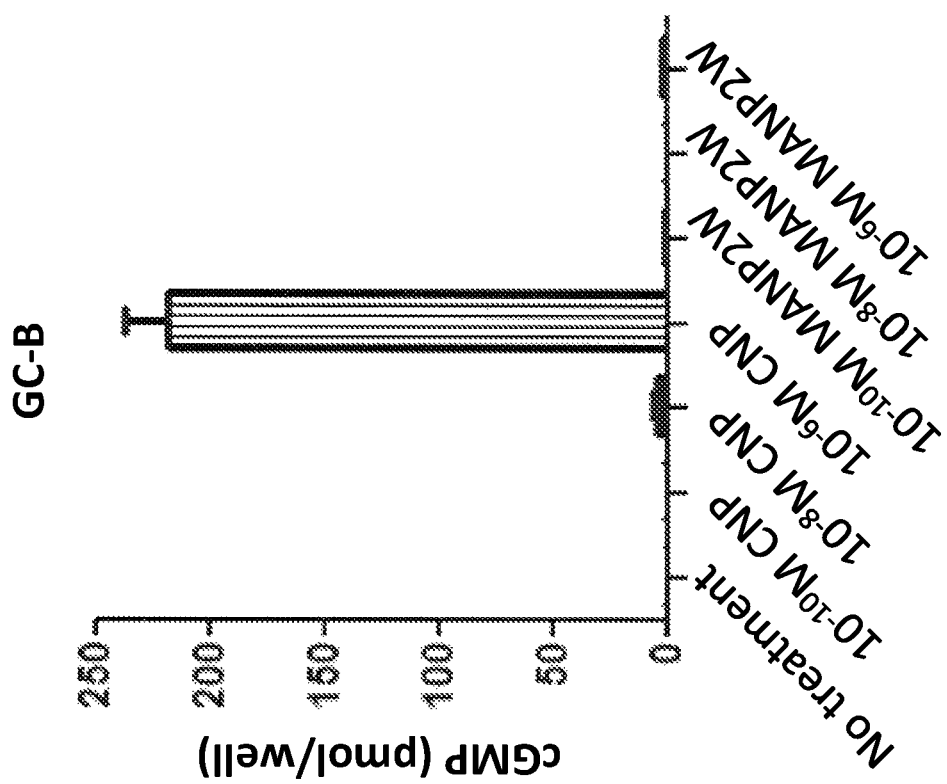

U/ml penicillin, 100 U/ml streptomycin, and 250 ug/ml G418, and were plated in 6-well plates. pGC-A-transfected cells were treated with MANP or MANP2W, while pGC-B-transfected cells were treated with CNP or MANP2W. Cells were incubated in Hank's balanced salt solution (Invitrogen; Carlsbad, Calif.) containing 20 mmol/L N-[2-hydroxyethyl]piperazine-N'[2-ethanesulfonic acid], 0.1% bovine serum albumin, and 0.5 mmol/L 3-isobutyl-1-methylzanthine (Sigma; St. Louis, Mo.). Treated cells received $10^{-6}$ M, $10^{-8}$ M, or $10^{-10}$ M of MANP, CNP, or MANP2W peptide for 10 minutes. After treatment, the cells were lysed in 300 ul 6% ice cold TCA and sonicated for 10 minutes, and the cell lysates were then centrifuged at 4° C., 12,000 g for 10 minutes. The supernatants were transferred to glass tubes and ether extracted four times in 4 volumes of ether, dried, and reconstituted in 300 ul cGMP assay buffer. The samples were assayed using a competitive radioimmunoassay cGMP kit (Perkin-Elmer; Boston, Mass.). These studies showed that MANP2W selectively activated pGC-A (FIG. 7A), as it did not activate pGC-B (FIG. 7B).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A natriuretic polypeptide comprising the amino acid sequence set forth in SEQ ID NO:5.

2. A natriuretic polypeptide comprising the amino acid sequence set forth in SEQ ID NO:3, or SEQ ID NO:6.

3. A natriuretic polypeptide comprising the amino acid sequence set forth in SEQ ID NO:15.

4. A pharmaceutical composition comprising a pharmaceutically acceptable carrier and the polypeptide of claim 1.

5. A pharmaceutical composition comprising a pharmaceutically acceptable carrier and the polypeptide of claim 2.

6. A pharmaceutical composition comprising a pharmaceutically acceptable carrier and the polypeptide of claim 3.

* * * * *

```
                         SEQUENCE LISTING

<160> NUMBER OF SEQ ID NOS: 15

<210> SEQ ID NO 1
    <211> LENGTH: 40
    <212> TYPE: PRT
    <213> ORGANISM: Homo sapiens

<400> SEQUENCE: 1

Ser Leu Arg Arg Ser Ser Cys Phe Gly Gly Arg Met Asp Arg Ile Gly
    1               5                   10                  15

Ala Gln Ser Gly Leu Gly Cys Asn Ser Phe Arg Tyr Arg Ile Thr Ala
                20                  25                  30

Arg Glu Asp Lys Gln Gly Trp Ala
            35                  40

<210> SEQ ID NO 2
    <211> LENGTH: 44
    <212> TYPE: PRT
    <213> ORGANISM: Artificial Sequence
    <220> FEATURE:
    <223> OTHER INFORMATION: synthetic

<400> SEQUENCE: 2

Thr Ala Pro Arg Ser Leu Arg Arg Ser Ser Cys Phe Gly Gly Arg Met
    1               5                   10                  15

Asp Arg Ile Gly Ala Gln Ser Gly Leu Gly Cys Asn Ser Phe Arg Tyr
                20                  25                  30

Arg Ile Thr Ala Arg Glu Asp Lys Gln Gly Trp Ala
            35                  40

<210> SEQ ID NO 3
    <211> LENGTH: 40
    <212> TYPE: PRT
    <213> ORGANISM: Artificial Sequence
    <220> FEATURE:
    <223> OTHER INFORMATION: synthetic

<400> SEQUENCE: 3

Ser Leu Lys Lys Ser Ser Cys Phe Gly Gly Arg Met Asp Arg Ile Gly
    1               5                   10                  15

Ala Gln Ser Gly Leu Gly Cys Asn Ser Phe Arg Tyr Arg Ile Thr Ala
                20                  25                  30

Arg Glu Asp Lys Gln Gly Trp Ala
            35                  40

<210> SEQ ID NO 4
```

```
<211> LENGTH: 40
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: D-form

<400> SEQUENCE: 4

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Lys Gln Gly Trp Ala
        35                  40

<210> SEQ ID NO 5
<211> LENGTH: 39
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: D-form

<400> SEQUENCE: 5

Ser Leu Arg Arg Ser Cys Phe Gly Gly Arg Met Asp Arg Ile Gly Ala
1               5                   10                  15

Gln Ser Gly Leu Gly Cys Asn Ser Phe Arg Tyr Arg Ile Thr Ala Arg
            20                  25                  30

Glu Asp Lys Gln Gly Trp Ala
        35

<210> SEQ ID NO 6
<211> LENGTH: 40
<212> TYPE: PRT
<213> ORGANISM: Artificial Sequence
<220> FEATURE:
<223> OTHER INFORMATION: synthetic

<400> SEQUENCE: 6

Thr Leu Arg Arg Thr Thr Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Lys Gln Gly Trp Ala
        35                  40

<210> SEQ ID NO 7
<211> LENGTH: 28
<212> TYPE: PRT
<213> ORGANISM: Homo sapiens

<400> SEQUENCE: 7

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 8
```

```
<211> LENGTH: 32
<212> TYPE: PRT
<213> ORGANISM: Homo sapiens

<400> SEQUENCE: 8

Ser Pro Lys Met Val Gln Gly Ser Gly Cys Phe Gly Arg Lys Met Asp
1               5                   10                  15

Arg Ile Ser Ser Ser Gly Leu Gly Cys Lys Val Leu Arg Arg His
            20                  25                  30

<210> SEQ ID NO 9
<211> LENGTH: 22
<212> TYPE: PRT
<213> ORGANISM: Homo sapiens

<400> SEQUENCE: 9

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 10
<211> LENGTH: 32
<212> TYPE: PRT
<213> ORGANISM: Homo sapiens

<400> SEQUENCE: 10

Thr Ala Pro Arg Ser Leu Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
            20                  25                  30

<210> SEQ ID NO 11
<211> LENGTH: 38
<212> TYPE: PRT
<213> ORGANISM: Dendroaspis angusticeps

<400> SEQUENCE: 11

Glu Val Lys Tyr Asp Pro Cys Phe Gly His Lys Ile Asp Arg Ile Asn
1               5                   10                  15

His Val Ser Asn Leu Gly Cys Pro Ser Leu Arg Asp Pro Arg Pro Asn
            20                  25                  30

Ala Pro Ser Thr Ser Ala
            35

<210> SEQ ID NO 12
<211> LENGTH: 12
<212> TYPE: PRT
<213> ORGANISM: Homo sapiens

<400> SEQUENCE: 12

Arg Ile Thr Ala Arg Glu Asp Lys Gln Gly Trp Ala
1               5                   10

<210> SEQ ID NO 13
<211> LENGTH: 93
<212> TYPE: DNA
<213> ORGANISM: Homo sapiens

<400> SEQUENCE: 13
agcctgcgga gatccagctg cttcggggggc aggatggaca ggattggagc ccagagcgga    60
ctgggctgta acagcttccg gtaccgaaga taa                                  93
```

<210> SEQ ID NO 14
<211> LENGTH: 123
<212> TYPE: DNA
<213> ORGANISM: Homo sapiens

<400> SEQUENCE: 14

```
agcctgcgga gatccagctg cttcgggggc aggatggaca ggattggagc ccagagcgga    60
ctgggctgta acagcttccg gtaccggata acagccaggg aggacaagca gggctgggcc   120
tag                                                                 123
```

<210> SEQ ID NO 15
<211> LENGTH: 41
<212> TYPE: PRT
<213> ORGANISM: Artificial Sequence
<220> FEATURE:
<223> OTHER INFORMATION: synthetic

<400> SEQUENCE: 15

```
Ser Trp Leu Arg Arg Ser Ser Cys Phe Gly Gly Arg Met Asp Arg Ile
1               5                   10                  15
Gly Ala Gln Ser Gly Leu Gly Cys Asn Ser Phe Arg Tyr Arg Ile Thr
            20                  25                  30
Ala Arg Glu Asp Lys Gln Gly Trp Ala
        35                  40
```